US011892000B2

(12) United States Patent
Kenyon et al.

(10) Patent No.: US 11,892,000 B2
(45) Date of Patent: Feb. 6, 2024

(54) COMPACT LOW NOISE EFFICIENT BLOWER FOR CPAP DEVICES

(71) Applicant: ResMed Motor Technologies Inc., Chatsworth, CA (US)

(72) Inventors: Barton John Kenyon, Sydney (AU); Peter John Sweeney, Sydney (AU)

(73) Assignee: ResMed Motor Technologies Inc., Chatsworth, CA (US)

( * ) Notice: Subject to any disclaimer, the term of this patent is extended or adjusted under 35 U.S.C. 154(b) by 0 days.

(21) Appl. No.: 17/752,992

(22) Filed: May 25, 2022

(65) Prior Publication Data

US 2022/0290677 A1    Sep. 15, 2022

Related U.S. Application Data

(60) Division of application No. 16/795,906, filed on Feb. 20, 2020, now Pat. No. 11,353,030, which is a (Continued)

(30) Foreign Application Priority Data

May 24, 2006    (AU) ................................ 2006902781

(51) Int. Cl.
  *F04D 17/16*    (2006.01)
  *F04D 25/06*    (2006.01)
  (Continued)

(52) U.S. Cl.
  CPC ....... *F04D 17/164* (2013.01); *A61M 16/0057* (2013.01); *A61M 16/0066* (2013.01);
  (Continued)

(58) Field of Classification Search
  CPC ...... F04D 17/164; F04D 17/12; F04D 17/122; F04D 17/16; F04D 17/165; F04D 25/06;
  (Continued)

(56) References Cited

U.S. PATENT DOCUMENTS 2,018,092 A    10/1935    Rickert
2,064,587 A    12/1936    Carlstedt
(Continued)

FOREIGN PATENT DOCUMENTS

AU    2003284610    7/2004
DE    196 26 896 A1    1/1998
(Continued)

OTHER PUBLICATIONS

First Examination Report issued in corresponding New Zealand Application No. 714602 dated Dec. 14. 2015
(Continued)

*Primary Examiner* — Eldon T Brockman
*Assistant Examiner* — Andrew J Marien
(74) *Attorney, Agent, or Firm* — Nixon & Vanderhye P.C.

(57) ABSTRACT

A blower for providing a supply of air at positive pressure in the range of approximately 2 cmH$_2$O to 30 cmH$_2$0 includes a motor, at least one impeller, and a stationary component. The stationary component includes an inlet and an outlet. The motor, the impeller, the inlet and outlet are co-axial.

24 Claims, 25 Drawing Sheets

Related U.S. Application Data continuation of application No. 15/594,096, filed on May 12, 2017, now Pat. No. 10,605,246, which is a continuation of application No. 14/252,915, filed on Apr. 15, 2014, now Pat. No. 9,677,563, which is a continuation of application No. 13/597,705, filed on Aug. 29, 2012, now Pat. No. 8,734,097, which is a continuation of application No. 12/926,657, filed on Dec. 2, 2010, now Pat. No. 8,267,648, which is a continuation of application No. 12/227,637, filed as application No. PCT/AU2007/000719 on May 24, 2007, now Pat. No. 7,866,944.

(51) Int. Cl.

| | | |
|---|---|---|
| *F04D 29/58* | (2006.01) | |
| *F04D 17/12* | (2006.01) | |
| *A61M 16/00* | (2006.01) | |
| *F04D 29/42* | (2006.01) | |
| *F04D 29/44* | (2006.01) | |
| *F04D 29/66* | (2006.01) | |
| *F04D 25/08* | (2006.01) | |
| *F04D 29/02* | (2006.01) | |
| *F04D 29/28* | (2006.01) | |

(52) U.S. Cl.
CPC .......... *F04D 17/12* (2013.01); *F04D 17/122* (2013.01); *F04D 17/16* (2013.01); *F04D 17/165* (2013.01); *F04D 25/06* (2013.01); *F04D 25/0606* (2013.01); *F04D 25/08* (2013.01); *F04D 29/023* (2013.01); *F04D 29/281* (2013.01); *F04D 29/4253* (2013.01); *F04D 29/441* (2013.01); *F04D 29/444* (2013.01); *F04D 29/5806* (2013.01); *F04D 29/667* (2013.01); *A61M 2205/42* (2013.01)

(58) Field of Classification Search
CPC .... F04D 25/0606; F04D 25/08; F04D 29/023; F04D 29/281; F04D 29/4253; F04D 29/441; F04D 29/444; F04D 29/667; F04D 29/5806; F04D 29/584; A61M 16/0057; A61M 16/0066; A61M 2205/42
See application file for complete search history.

(56) References Cited

U.S. PATENT DOCUMENTS

| | | | |
|---|---|---|---|
| 2,328,038 A | 8/1943 | Taylor | |
| 2,336,716 A | 12/1943 | Clements | |
| 2,562,996 A | 8/1951 | Winthrop | |
| 2,726,807 A | 12/1955 | Lewis | |
| 2,822,123 A | 2/1958 | Cole | |
| 2,857,849 A | 10/1958 | Pezzillo | |
| 3,083,308 A | 3/1963 | Baumann | |
| 3,102,679 A | 9/1963 | Emil | |
| 3,171,353 A * | 3/1965 | McMahan | F04D 29/5806 |
| | | | 415/199.3 |
| 3,243,102 A | 3/1966 | McMAHAN | |
| 3,245,610 A | 4/1966 | Sebok et al. | |
| 3,628,882 A | 12/1971 | Nilsson | |
| 3,791,772 A | 2/1974 | Keimpema et al. | |
| 4,111,615 A | 9/1978 | Watanabe | |
| RE32,027 E | 11/1985 | Hyatt et al. | |
| 4,647,271 A | 3/1987 | Nagai | |
| 4,669,952 A | 6/1987 | Forsyth et al. | |
| 4,944,310 A | 7/1990 | Sullivan | |
| 4,946,348 A | 8/1990 | Yapp | |
| 4,966,532 A | 10/1990 | Fengsheng | |
| 4,969,803 A | 11/1990 | Turanskyj | |
| 5,296,769 A | 3/1994 | Havens et al. | |
| 5,308,224 A | 5/1994 | Olivero | |
| 5,344,285 A | 9/1994 | O'Sullivan et al. | |
| 5,478,215 A | 12/1995 | Kobayashi et al. | |
| 5,584,286 A | 12/1996 | Kippax | |
| 5,810,557 A * | 9/1998 | Akinkuotu | F04D 17/165 |
| | | | 415/206 |
| 5,888,053 A | 3/1999 | Kobayashi et al. | |
| 6,349,724 B1 | 2/2002 | Burton et al. | |
| 6,425,739 B1 | 7/2002 | Ambler | |
| 6,511,298 B2 | 1/2003 | Takura | |
| 6,558,120 B2 * | 5/2003 | Kim | F04D 29/281 |
| | | | 416/189 |
| 6,622,724 B1 * | 9/2003 | Truitt | A61M 16/022 |
| | | | 128/204.18 |
| 6,666,660 B2 | 12/2003 | Kegg | |
| 6,763,828 B2 | 7/2004 | Arnott | |
| 6,769,876 B2 * | 8/2004 | Sakai | F01D 1/02 |
| | | | 415/206 |
| 6,844,638 B2 | 1/2005 | Vasilescu | |
| 6,848,887 B2 * | 2/2005 | Kim | F04D 29/282 |
| | | | 249/59 |
| 6,881,033 B2 | 4/2005 | Makinson et al. | |
| 6,910,483 B2 | 6/2005 | Daly et al. | |
| 7,021,905 B2 | 4/2006 | Torrey | |
| 7,025,576 B2 | 4/2006 | Chaffee | |
| 7,121,799 B2 | 10/2006 | Kim et al. | |
| 7,163,372 B2 | 1/2007 | Kegg | |
| 7,866,944 B2 | 1/2011 | Kenyon et al. | |
| 8,267,648 B2 | 9/2012 | Kenyon et al. | |
| 8,734,097 B2 | 5/2014 | Kenyon et al. | |
| 9,677,563 B2 | 6/2017 | Kenyon et al. | |
| 10,605,246 B2 | 3/2020 | Kenyon et al. | |
| 2002/0028138 A1 * | 3/2002 | Lee | F04D 29/281 |
| | | | 415/206 |
| 2002/0106277 A1 * | 8/2002 | Chapman | F04D 29/4233 |
| | | | 415/206 |
| 2003/0168064 A1 | 9/2003 | Daly et al. | |
| 2003/0206800 A1 * | 11/2003 | Mathson | F04D 29/30 |
| | | | 415/220 |
| 2003/0209024 A1 * | 11/2003 | Lee | F04D 17/165 |
| | | | 62/262 |
| 2005/0005606 A1 * | 1/2005 | Vrbas | F01D 5/045 |
| | | | 60/612 |
| 2005/0163614 A1 * | 7/2005 | Chapman | F04D 29/30 |
| | | | 415/206 |
| 2005/0186077 A1 * | 8/2005 | Lee | F04D 29/281 |
| | | | 416/179 |
| 2006/0150973 A1 | 7/2006 | Chalvignac | |
| 2009/0246013 A1 | 10/2009 | Kenyon et al. | |
| 2011/0073110 A1 | 3/2011 | Kenyon et al. | |
| 2013/0028710 A1 | 1/2013 | Kenyon et al. | |
| 2014/0227091 A1 | 8/2014 | Kenyon et al. | |
| 2017/0248144 A1 | 8/2017 | Kenyon et al. | |
| 2020/0182250 A1 | 6/2020 | Kenyon et al. | |

FOREIGN PATENT DOCUMENTS

| | | |
|---|---|---|
| EP | 0385298 | 9/1990 |
| EP | 0694698 | 4/1998 |
| GB | 1 160 136 A | 7/1969 |
| GB | 1271808 | 4/1972 |
| GB | 2118627 | 11/1983 |
| GB | 2 166 494 | 5/1986 |
| JP | S38-024773 | 11/1963 |
| JP | 49-008961 | 3/1974 |
| JP | S51-9049 | 3/1976 |
| JP | S52-17334 | 2/1977 |
| JP | S53-112805 | 9/1978 |
| JP | S59-213994 | 12/1984 |
| JP | S62-197696 | 9/1987 |
| JP | S63-170595 | 7/1988 |
| JP | 64-41699 | 2/1989 |
| JP | H01-041699 | 2/1989 |
| JP | H05-288195 | 11/1993 |
| JP | H05-296193 | 11/1993 |
| JP | H08-093683 | 4/1996 |
| JP | 2000-130809 | 5/2000 |
| JP | 2001-286565 | 10/2001 |
| JP | 2003-214395 | 7/2003 |
| WO | PCT/US98/19635 | 9/1998 |

(56) References Cited

FOREIGN PATENT DOCUMENTS

| WO | PCT/AU99/00444 | 6/1999 |
|---|---|---|
| WO | WO 2000/027021 | 5/2000 |
| WO | WO 2004/108198 | 12/2004 |
| WO | WO 2005/002655 | 1/2005 |
| WO | PCT/AU2006/001616 | 10/2006 |
| WO | PCT/AU2006/001617 | 10/2006 |

OTHER PUBLICATIONS

International Search Report for PCT/AU2007/000719, dated Aug. 8, 2007.
European Extended Search Report issued in EP07718965.2, dated Oct. 23, 2009.
Notice of Acceptance issued in Australian Patent Application No. 2007252223, dated April 14, 2009.
Office Action issued in related Chinese Appln. No. 200780018828.8, dated May 26, 2010, with English translation.
Examination Report issued in New Zealand Appln. No. 589602, dated Dec. 6, 2010.
Second Office Action issued in related Chinese Appln. No. 2007800188288, dated Jan. 20, 2012.
Office Action issued in related Japanese Appln. No. 2009-511305, dated May 8, 2012, with English translation.
Office Action issued in corresponding Chinese Appin. No. 2007800188288, dated Sep. 4, 2012, with English translation thereof.
Office Action issued in corresponding Japanese appln. No. 2009-511305, dated Feb. 5, 2013, with English translation thereof.
First Examination Report issued in corresponding New Zealand Appln. No. 604972 dated Jan. 9, 2013.
Notice of Allowance issued in corresponding Japanese Appln. No. 2009-511305 dated Oct. 15, 2013, with English translation thereof.
Office Action issued in corresponding Japanese Appln. No. 2012-175625 dated Oct. 1, 2013, with English translation thereof.
Office Action issued in corresponding Chinese Appln. No. 2013100662318 dated February 26, 2014, with English translation thereof.
U.S. Appl. No. 60/853,778 filed Oct. 2006, Sears.
Notice of Allowance issued in corresponding Japanese Appln. No. 2014-028229 dated Feb. 2, 2015, with English language translation thereof.
Notification of Acceptance of a Request for Invalidation issued in Chinese Patent No. 2007800188288 dated Ma. 30, 2015, with English translation thereof.
Third Office Action issued in corresponding Chinese Appln. No. 2013100662318 dated Apr. 3, 2015, with English ranslation thereof.
Extended European Search Report in EP 12 15 8135.9, dated Jul. 24, 2014.
Extended European Search Report in EP 11 15 53 92. 1, dated Jul. 24, 2014.
Further Examination Report issued in corresponding New Zealand Appln. No. 617659 dated Feb. 16, 2015.
Communication dated Jul. 27, 2018 issued in European Application No. 11155392.1 (5 pages).
Administrative Judgment of Beijing Intellectual Property Court of the People's Republic of China dated Jul. 17, 2018 issued in Chinese Application No. 200780018828.8 with English translation (38 pages).
Communication dated Aug. 8, 2018 issued in European Application No. 121581359 (5 pages).
Kenyon et al., U.S. Appl. No. 16/795,906, filed Feb. 20, 2020, for "Compact Low Noise Efficient Blower for CPAP Devices," (parent application).

\* cited by examiner

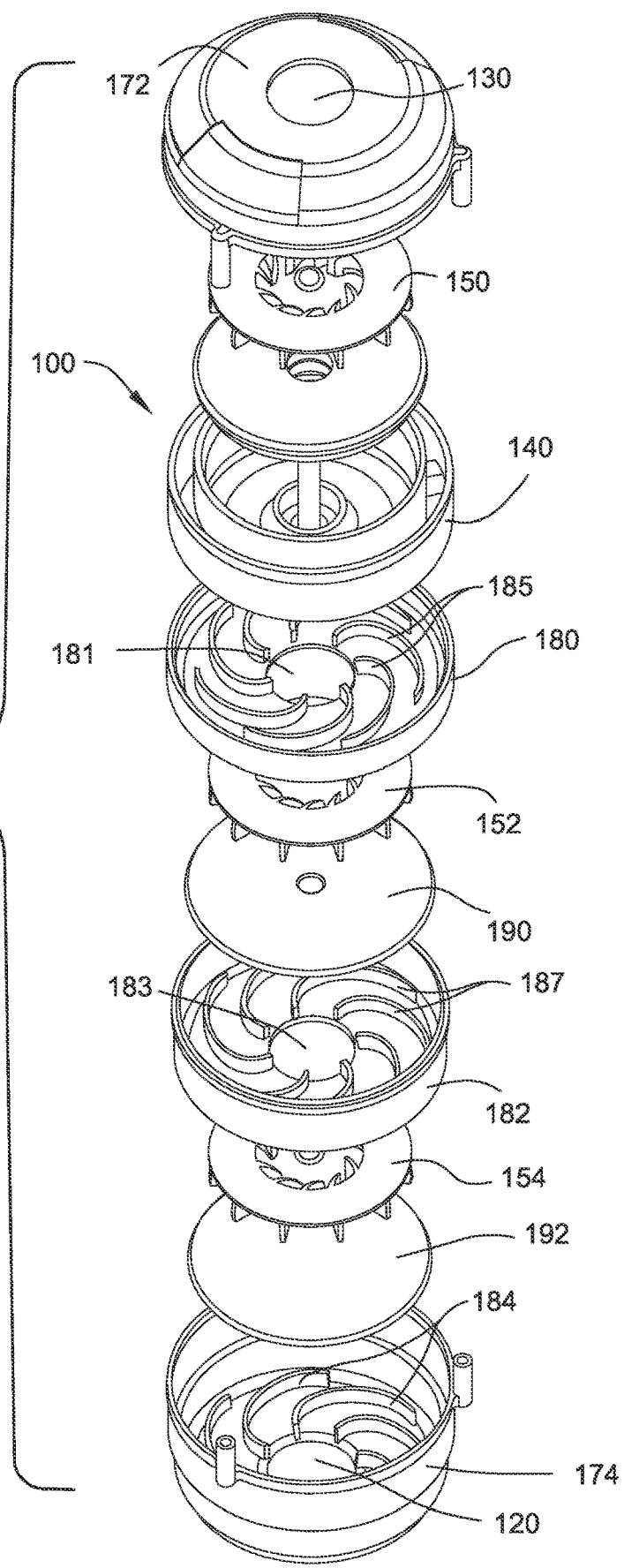

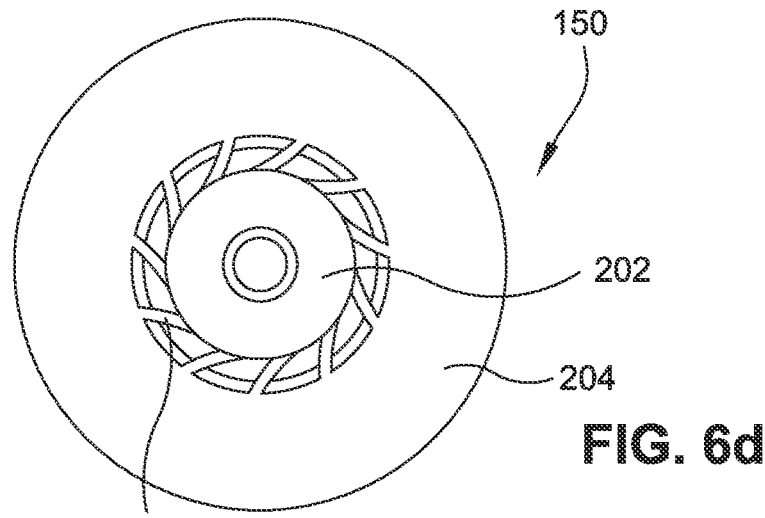
FIG. 6d
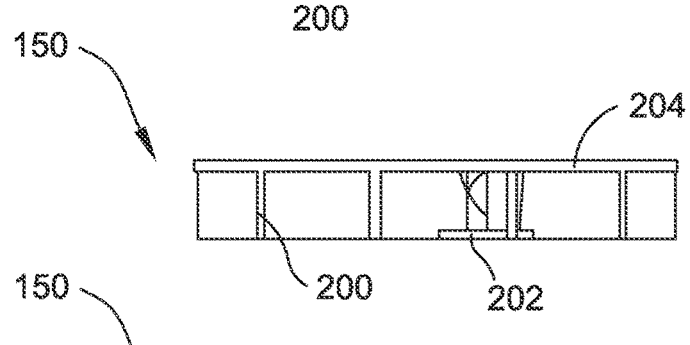
FIG. 6e
FIG. 6f
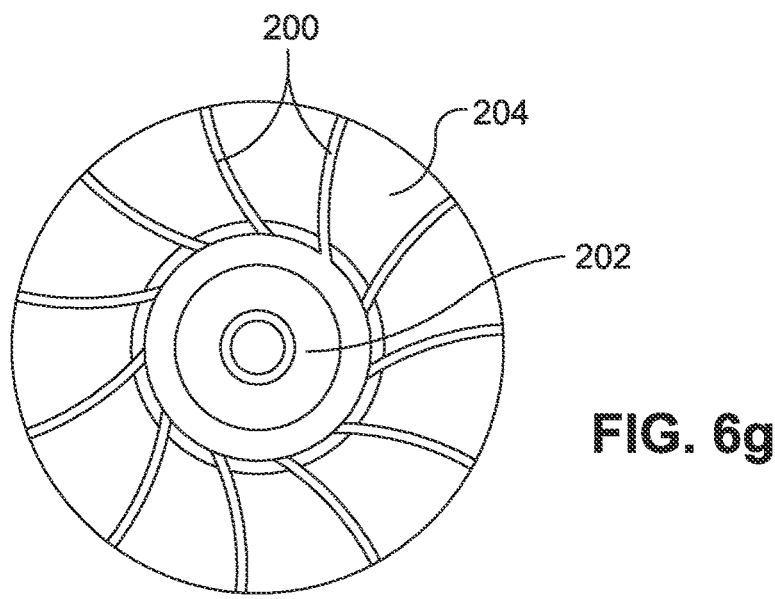
FIG. 6g

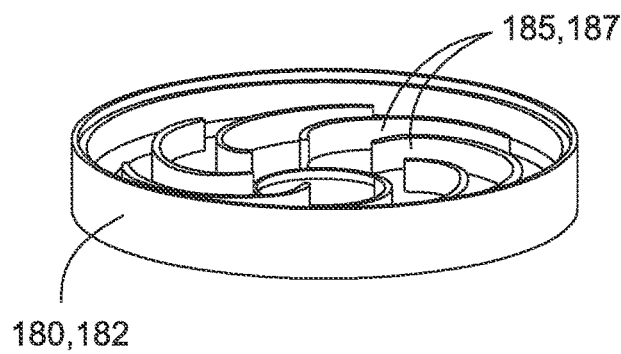
FIG. 7a
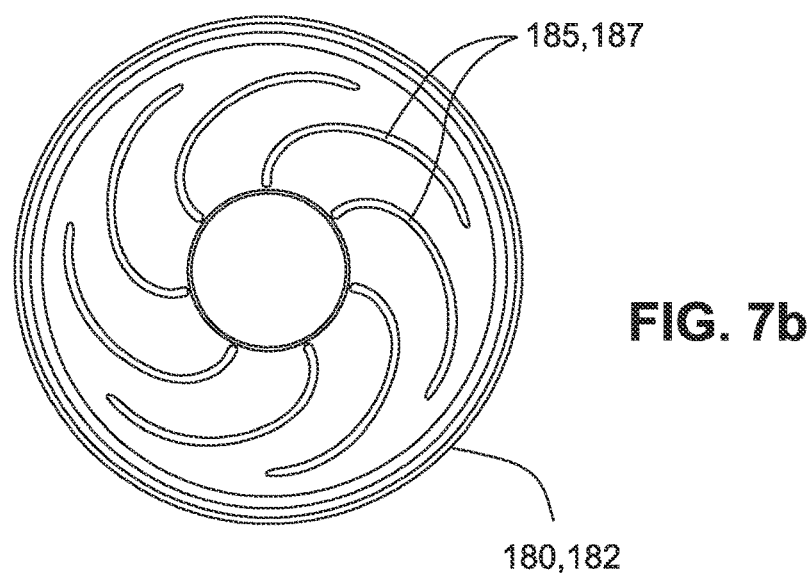
FIG. 7b
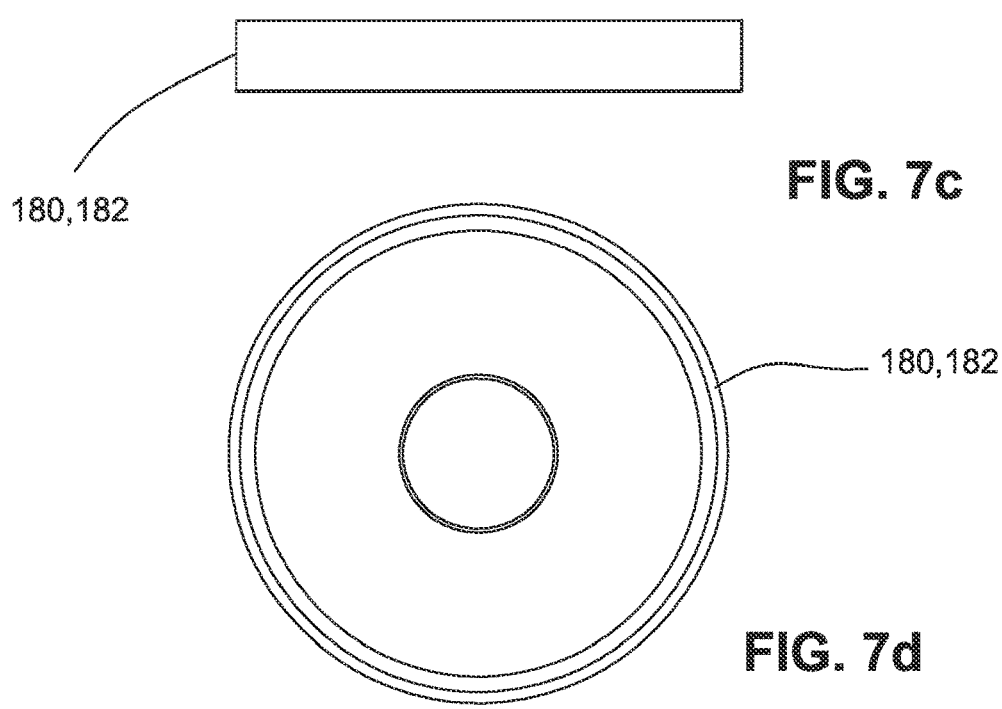
FIG. 7c
FIG. 7d ial of U.S. patent application
COMPACT LOW NOISE EFFICIENT BLOWER FOR CPAP DEVICES

CROSS-REFERENCE TO RELATED APPLICATIONS

This application is a divisional of U.S. patent application Ser. No. 16/795,906, filed Feb. 20, 2022, which is a continuation of U.S. patent application Ser. No. 15/594,096, filed May 12, 2017, now U.S. Pat. No. 10,605,246, which is a continuation of U.S. patent application Ser. No. 14/252,915, filed Apr. 15, 2014, now U.S. Pat. No. 9,677,563, which is a continuation of U.S. patent application Ser. No. 13/597,705, filed Aug. 29, 2012, now U.S. Pat. No. 8,734,097, which is a continuation of U.S. patent application Ser. No. 12/926,657, filed Dec. 2, 2010, now U.S. Pat. No. 8,267,648, which is a continuation of U.S. patent application Ser. No. 12/227,637, filed Nov. 24, 2008, now U.S. Pat. No. 7,866,944, which is the U.S. National Phase of International Application No. PCT/AU2007/000719, filed May 24, 2007, which claims the benefit of Australian Provisional Application No. AU 2006902781, filed May 24, 2006, each of which is incorporated herein by reference in its entirety.

FIELD OF THE INVENTION

The invention relates to an efficient, low-noise, compact blower. The blower may be used in a range of devices including medical, cleaning, automotive or computer devices. The blower may also be used as an extractor or suction device. In an embodiment, the blower may be used in a non-invasive ventilation (NIVV) device such as a CPAP or ventilator device.

BACKGROUND OF THE INVENTION

Nasal CPAP Treatment of OSA

Nasal Continuous Positive Airway Pressure (CPAP) treatment of Obstructive Sleep Apnea (OSA) was invented by Sullivan. See U.S. Pat. No. 4,944,310. Apparatus for treating OSA typically comprises a blower that provides a supply of air or breathable gas to a patient interface, such as a mask, via an air delivery conduit. Since patients typically sleep while wearing the device, it is desirable to have a system which is quiet and comfortable.

Generic Blower/Air Pump

Blowers are typically classified as centrifugal, axial or mixed flow. Generally, blowers comprise two main parts: a rotating part, namely an impeller and shaft; and a stationary part that defines a fluid flow path, typically a chamber such as a volute. Rotation of the impeller imparts kinetic energy to the air. The stationary part redirects the air expelled from the impeller into an enclosed outlet passage. During this redirection, resistance is encountered to flow because of the pressure generated by downstream resistance or a downstream pressure source. As the flow is slowed against this resistance, a portion of the kinetic energy is converted to potential energy in the form of pressure.

Generally, the faster the impeller is rotated, the higher the pressure that will be developed. A less effective blower must rotate its impeller faster to generate the same pressure as a more effective blower. Generally, running a given blower slower makes it quieter and prolongs its life. Hence, it is generally desirable to make blowers more effective at generating a supply of air at positive pressure.

With reference to FIGS. 1 and 2, three directions are defined, i.e., radial R, tangential T and axial A. Prior art centrifugal blower 10 includes an outlet 20, an inlet 30, an electric motor 40, an impeller 50 and a shaft 60. Arrows 70 indicate the general direction of airflow. Air enters the blower at the inlet 30 and is accelerated by the rotating impeller. The rotation imparted by the impeller generally directs the airflow in a tangential direction T. The volute then constrains the airflow to spiral the volute. The airflow then exits the blower in a generally tangential direction T via the outlet 20.

In some blowers, such as axially developed volute blowers, the volute geometry directs the tangential spiraling airflow in a slight axial direction A prior to exiting the blower in a generally tangential direction T.

The performance of a blower is often described using fan curves, which show the flow rate of air versus outlet pressure of air. Many factors affect the fan curve including impeller diameter and the number and shape of the impeller blades. The design process is a complex balance between competing priorities such as desired pressure, flow rate, size, reliability, manufacturability and noise. While many combinations of size, shape and configuration of components may produce a flow of pressurized air, such a result may be far from optimal, or be impractical.

ResMed Axial Volute Design

Another form of known blower design is described in ResMed's International Patent Application PCT/AU99/00444, published as WO 99/64747, the contents of which are hereby expressly incorporated by reference. As described in this patent application, the volute geometry develops in a generally axial direction, however air exits this blower in a generally tangential direction.

Respironics Ventilator

Respironics International Patent Application PCT US98/19635, published as WO 99/13932, describes a medical ventilator which has a blower assembly that preferably includes three rotating impellers and two stationary stators. In this device, a conventional volute design is used such that air exits the blower assembly in a generally tangential direction.

A disadvantage of this blower design is it tends to suffer from blade pass tonal noise emission.

Respironics REMstar

Another known blower is found in the Respironics REMstar series of CPAP devices. In this device, air exits the blower in a generally tangential direction.

ResMed Blowers

U.S. Pat. No. 6,910,483 (Daly et al) assigned to ResMed Limited describes a double ended variable speed blower for Continuous Positive Airway Pressure (CPAP) ventilation of patients that includes two impellers in the gas flow path that cooperatively pressurize gas to desired pressure and flow characteristics. The contents of this patent are hereby expressly incorporated by reference. In this device, air exits the blower in a generally tangential direction.

PCT Application Nos. PCT/AU2006/001617, filed Oct. 27, 2006, and PCT/AU2006/001616, filed Oct. 27, 2006, describe multiple stage blowers. The contents of both of these PCT applications are hereby incorporated by reference.

As noted above, known CPAP and VPAP blowers use a more or less conventional volute design, namely one where the air leaves the volute tangentially. These designs have the disadvantage that the asymmetry of the volute leads to asymmetry of flow patterns in the volute and impeller. This problem is especially significant at flow rates away from the ideal "design" flow rates of the volute. CPAPs and VPAPs, unfortunately, are used for a substantial portion of their operational time under non-ideal flow conditions as a consequence of very high excursions in the flow demand. This means that the flow patterns within the volute, and consequently within the impeller, become highly asymmetrical, uneven, and even unstable. This in turn leads to pressure pulses and turbulence. As a consequence, acoustic blade pass tonal noise and turbulence noise are produced.

SUMMARY OF THE INVENTION

A first aspect of the invention is directed to a respiratory device that quietly and effectively provides a supply of air at positive pressure. Another aspect of the invention is to provide a blower for a NIVV device for use in treatment of a range of respiratory diseases. Another aspect of the invention is to achieve a large pressure delivery for a given motor speed. Another aspect of the invention is a blower that can supply a given pressure at a relatively low motor speed and with a fast response time. Another aspect of the invention is a blower that has reduced blade pass tonal noise emission and/or turbulence noise emission.

In one form of the invention suitable for respiratory devices, the blower is configured to provide air pressurized in the range of 2 cm $H_2O$ to 100 cm $H_2O$. In another form suitable for treatment of Sleep Disordered Breathing, the blower is configured to provide pressure in the range of 2 cm $H_2O$ to 30 cm $H_2O$.

In one form, the blower is configured to provide air at flow rates up to 200 L/min. In one form, the blower is configured to provide air at flow rates ranging −50 L/min to +200 L/min.

In one form of the invention suitable for respiratory devices, the blower comprises at least one impeller having a relatively small diameter, for example in the range of 20 to 200 mm. In an embodiment, the impeller comprises two differently sized shrouds to provide a rigid impeller with relatively low inertia. The impeller may be injection molded from plastic such as polycarbonate or polypropylene.

An aspect of the invention is that the stationary portion of the blower defines an airflow path that is quiet and efficient. In an embodiment, the stationary portion defines an airflow path that is substantially axially symmetrical.

An aspect of the present invention has a stationary portion or volute design that is substantially axially symmetric on all stages. So no matter what the flow rate, the air feed pattern through the impeller blade passages, and in the volute, remains symmetrical and steady. This leads to lower strength pressure pulses and less turbulence, which in turn lead to lower levels of acoustic blade pass tone, and lower levels of turbulence noise.

In one form, the blower has one stage. In other forms of the invention, the blower has more than one stage. In forms of the invention where multiple stages are used along an axis, the motor may be positioned in the center and similar numbers of impellers may be positioned on either side of the motor along the axis.

In an embodiment, the stationary component of the blower includes a vane structure that receives airflow from an impeller and directs it in a radial direction. In an embodiment, the blower includes a shield positioned between an impeller and a vane structure to direct airflow to the stator inlet vanes in an orientation favorable to minimize losses and turbulence. In an embodiment, the airflow is directed in an axial direction between the impeller and vane structure. In an embodiment, the shield also presents a barrier between the impeller blades and the stator vane leading edges such that impeller blade pressure pulses are substantially isolated from the stator vanes.

Another aspect of the invention relates to a blower for supplying air at positive pressure including a stationary portion including an inlet and an outlet, a rotating portion provided to the stationary portion, and a motor adapted to drive the rotating portion. The inlet and outlet are co-axially aligned along an axis of the stationary portion such that air enters and exits the stationary portion in a generally axial direction.

Another aspect of the invention relates to a method for supplying air at positive pressure to a patient for treatment including providing air to a blower via an inlet that is axially aligned with an axis of the blower, directing the air through one or more stages of the blower, and supplying the air at positive pressure via an outlet that is axially aligned with the inlet.

Another aspect of the invention relates to a blower for supplying air at positive pressure including a stationary portion including an inlet and an outlet, a rotating portion provided to the stationary portion, and a motor adapted to drive the rotating portion. The stationary portion includes a shield to isolate stator vanes of the stationary portion from impeller blades of the rotating portion. The shield includes a tube portion having an interior surface and an exterior surface. The interior surface is adapted to support a bearing of the rotating portion and the exterior surface is adapted to support a stator assembly of the motor.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIGS. 4a to 4c show various exploded views of the blower shown in FIGS. 3a-3g;

FIGS. 6a to 6g show various views of an impeller according to an embodiment of the invention;

FIGS. 7a to 7d show various views of a stator component according to an embodiment of the invention;

DETAILED DESCRIPTION OF ILLUSTRATED EMBODIMENTS

Figure 1:
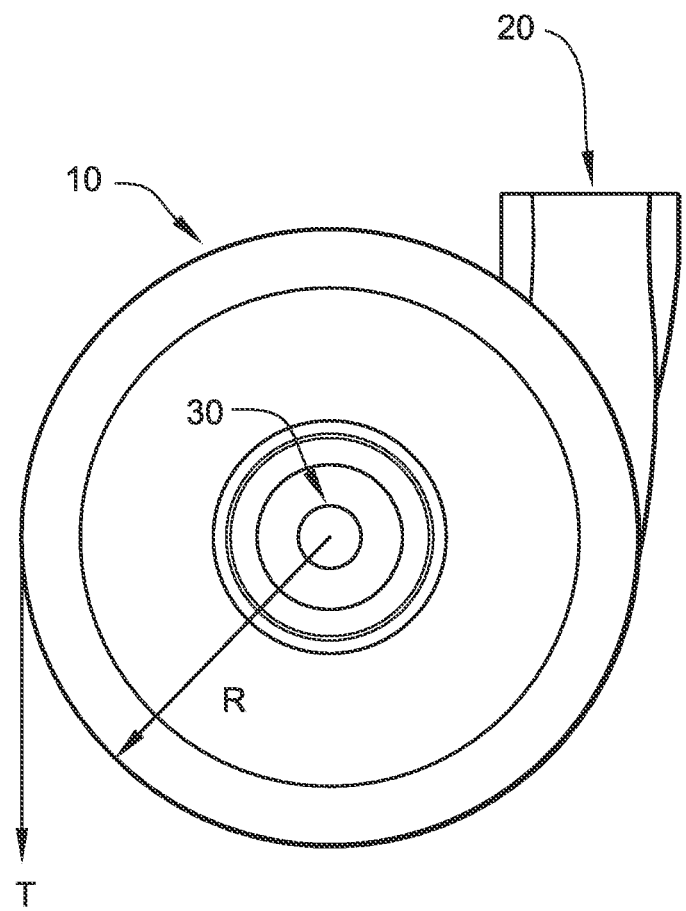
FIG. 1 shows a plan view of a generic prior art blower assembly.
Figure 2:
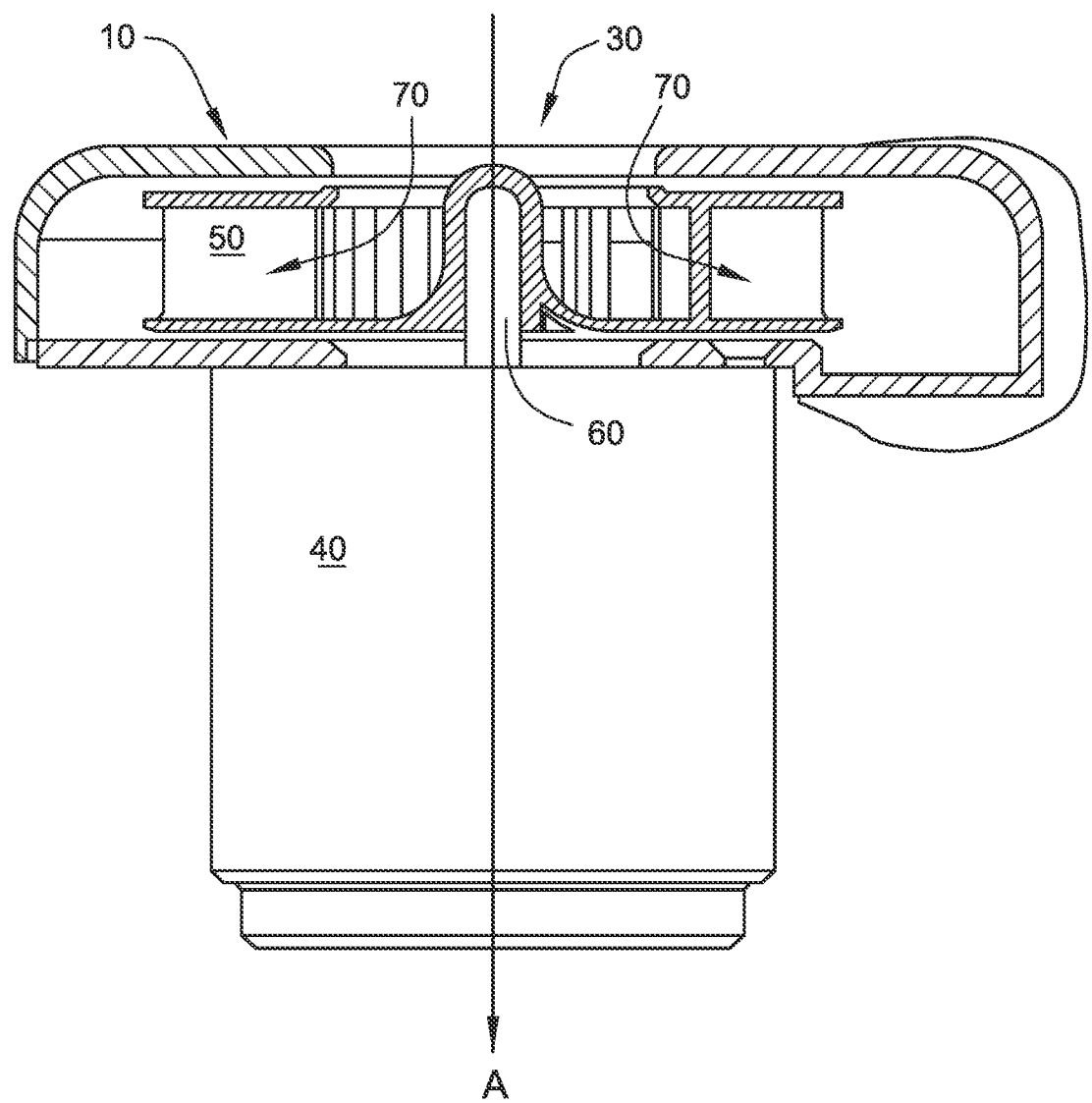
FIG. 2 shows an elevation view of the generic prior art blower assembly shown in FIG. 1.
Figure 3A:
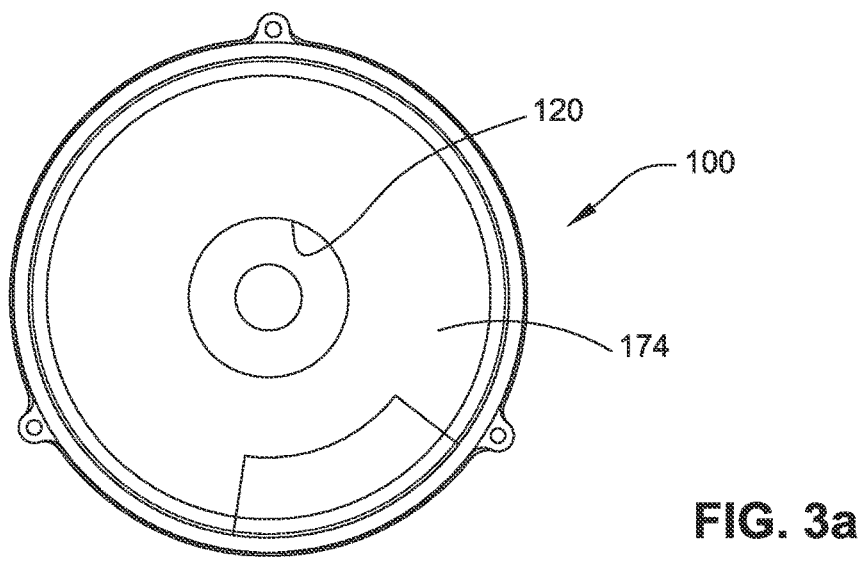
FIGS. 3a to 3g show various views of a blower according to an embodiment of the invention.
Figure 3B:
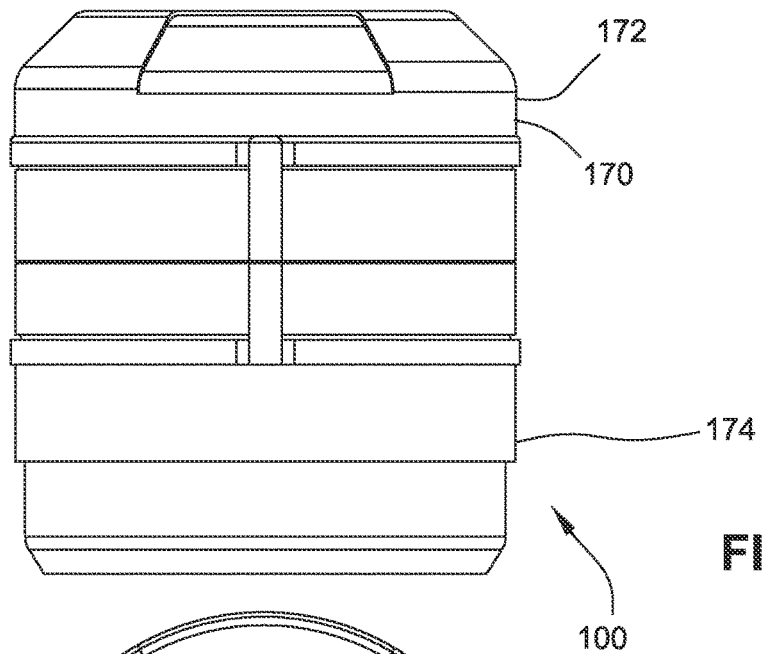
Figure 3C:
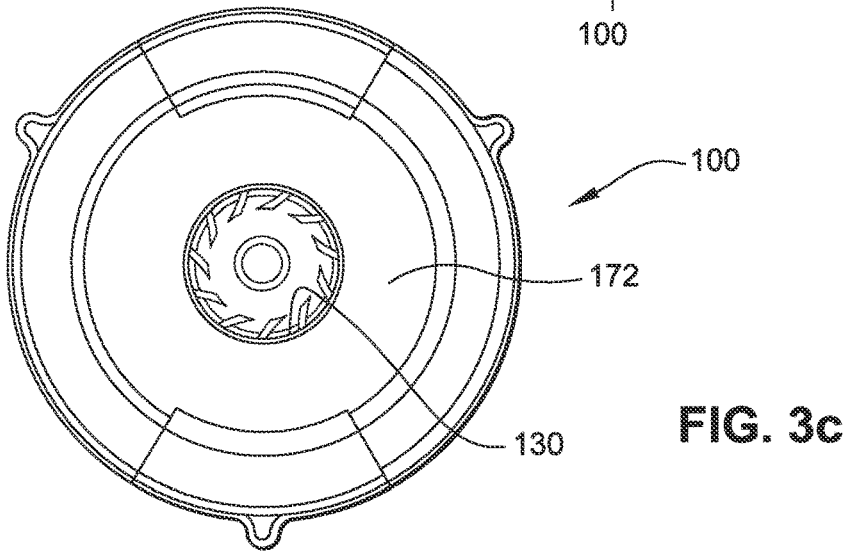
Figure 3D:
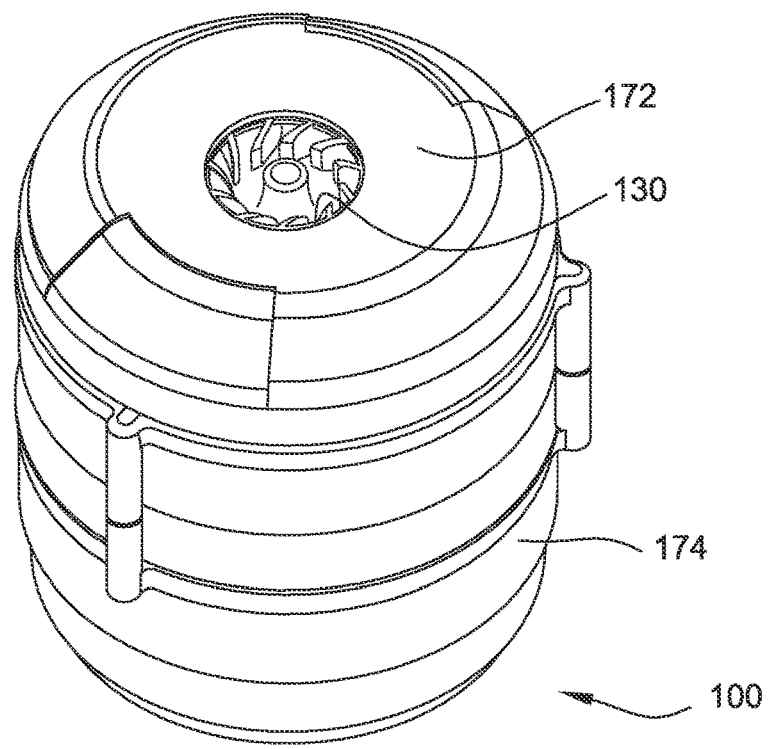
Figure 3E:
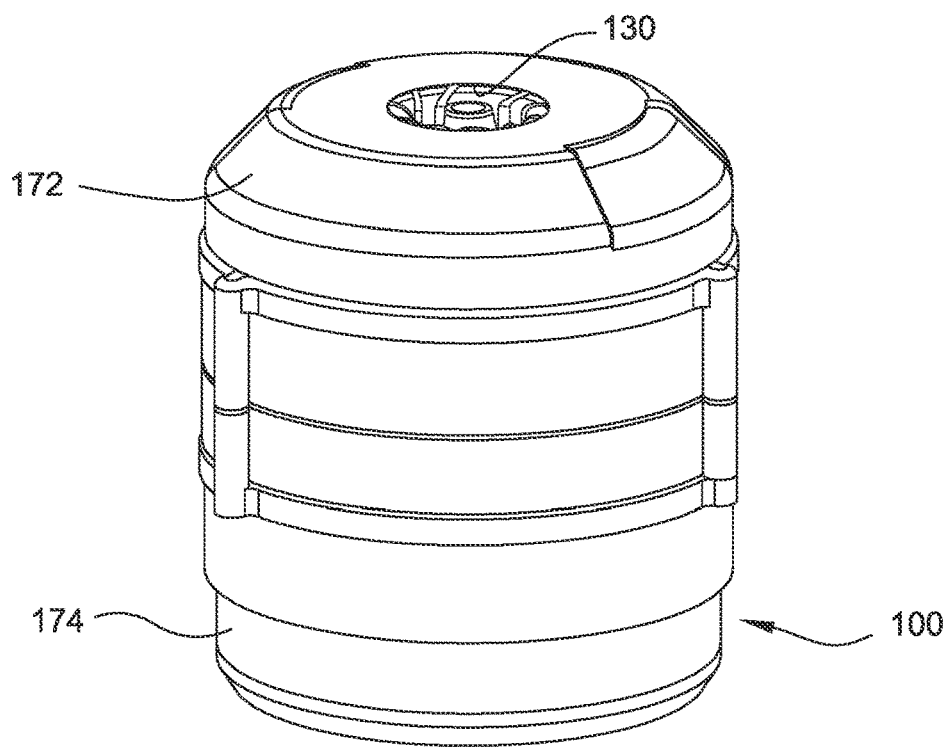
Figure 3F:
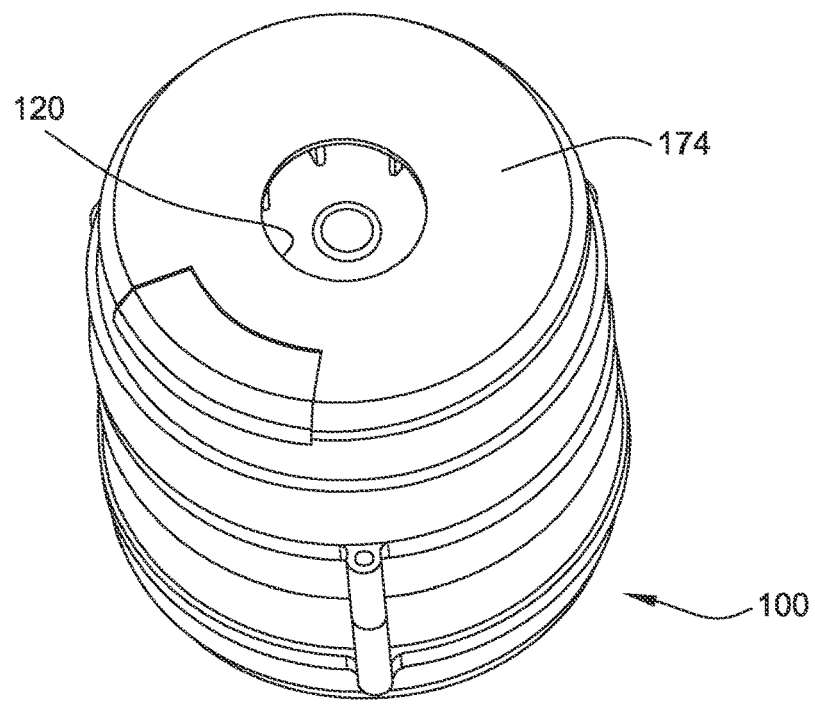
Figure 3G:
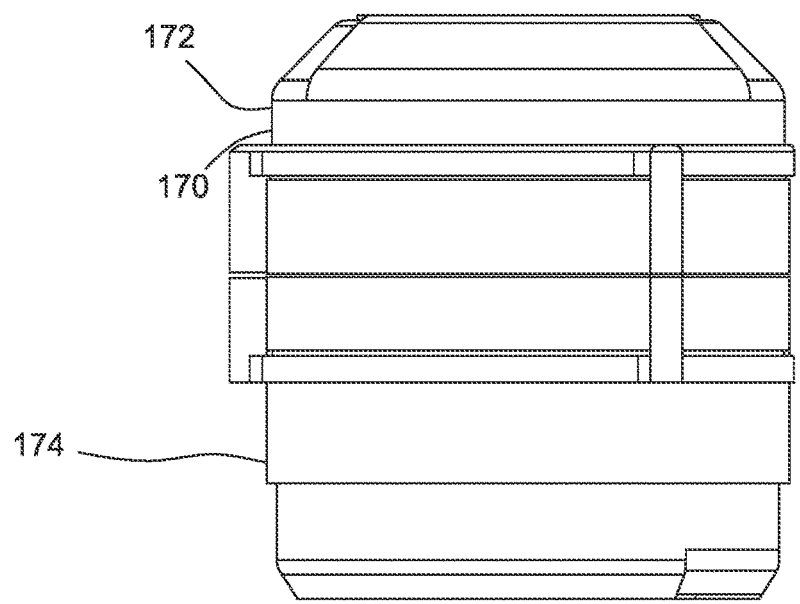

Aspects of the invention will be described herein in its application to non-invasive ventilation (NIVV) treatment apparatus (e.g., positive airway pressure (PAP) devices or flow generators), such as CPAP, mechanical ventilation and assisted respiration, but it is to be understood that the features of the invention will have application to other fields of application where blowers are used, such as vacuum cleaners, cooling equipment in computers and HVAC devices such as those found in buildings and vehicles.

In this specification, the words "air pump" and "blower" may be used interchangeably. In this specification, the phrase "stationary part" will be taken to include "volute". The term "air" will be taken to include breathable gases, for example air with supplemental oxygen. It is also acknowledged that the blowers described herein may be designed to pump fluids other than air.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

While particular embodiments of this invention have been described, it will be evident to those skilled in the art that the present invention may be embodied in other specific forms without departing from the essential characteristics thereof. The present embodiments and examples are therefore to be considered in all respects as illustrative and not restrictive, the scope of the invention being indicated by the appended claims rather than the foregoing examples or description, and all changes which come within the meaning and range of equivalency of the claims are therefore intended to be embraced therein. It will further be understood that any reference herein to known prior art does not, unless the contrary indication appears, constitute an admission that such prior art is commonly known by those skilled in the art to which aspects of the invention relate.

1. General Description

A blower 100 according to an embodiment of the invention may be in the form of a centrifugal air pump comprising a stationary portion, a rotating portion and an electric motor.

In an exemplary embodiment as shown in FIGS. 3a-5g, the stationary portion includes an external housing 170 in two parts 172, 174 and an assembly of internal flow directing components including three sets of stator components 180, 182, 184 and two shields 190, 192. The rotating portion comprises three impellers 150, 152, 154 and a shaft 160 adapted to be driven by electric motor 140. In an embodiment, the electric motor 140 may be a brushless D.C. motor. In the illustrated embodiment, the blower has three stages each with a corresponding impeller and set of stationary vanes and shields. As shown in FIGS. 3a-3g and 4a, the blower 100 is generally cylindrical and has an inlet 130 at one end and an outlet 120 at the other end.

In the illustrated embodiment, all the components of the blower are aligned along the shaft of the motor which defines an axis about which all components are generally symmetric. In an embodiment, the blower may be self similar sector-wise about its axis. This axial symmetry may apply to all stages.

An advantage of the blower according to an embodiment of the present invention is that it promotes symmetrical and stable flow patterns within the volute over the range of pressures and flow rates encountered during use. Thus, blade pass tone and turbulence noise emissions are reduced.

An advantage of the illustrated embodiment is the ease of manufacture and of assembly offered by the component geometry, particularly if injection molded, and by the stacked nature of the assembly.

2. Fluid Flow Path

2.1 First Stage

The first stage of the blower will now be described. As best shown in FIGS. 4a-4c and 5a-5g, air enters the blower 100 at the inlet 130 and passes into the first rotating impeller 150 where it is accelerated tangentially and directed radially outward. It then passes around the sides of the motor 140 flowing in a spiral manner with a large tangential velocity component and also an axial component towards the first set of stator vanes 185 in stator component 180. In this embodiment, no shield is provided for the first stage since the shielding function is provided by the motor case. At the first set of stator vanes 185, air is directed radially inwardly towards orifice 181, and thereafter onto the second stage.

2.2 Second Stage

In the second stage, as shown in FIGS. 4a-4c and 5a-5g, air is first accelerated tangentially by second rotating impeller 152 and also flows outwardly in a radial direction. Air then flows in a spiral manner with a large tangential velocity component and also an axial component passing through the gap 164 defined by the outer edge of circular disc 190 and the inner surface of the stator component 182. Air then enters the second set of stator vanes 187 formed in stator component 182 and is directed radially inwardly towards orifice 183, and thereafter onto the third stage.

2.3 Third Stage

The fluid flow path in the third stage is similar to the fluid flow path in the second stage. As shown in FIGS. 4a-4c and 5a-5g, air enters the stage via orifice 183 and is accelerated tangentially and also directed outwardly in a radial direction by third rotating impeller 154. Air then flows in a spiral manner with a large tangential component and also an axial component passing through the gap 166 defined by the outer edge of circular disc 192 and the inner edge of the housing 174. The air then is directed by stator vanes 184 formed in the housing 174 towards the outlet 120.

3. Stationary Portion

3.1 General

The stationary portion of the blower includes the two external housing parts 172, 174, the internal flow directing stator components 180, 182, 184 and two shields 190, 192 and may be made from any suitable rigid or semi-rigid material that is dimensionally stable. In an embodiment, the stator component may be made from material that provides one or more of the following characteristics: good thermal conductivity; relatively low cost; low density; acoustic dampening properties; and ease of molding to reduce post machining. The use of thermally conductive material may also assist in keeping the motor cool and warming the air. The ability to heat the air may provide an additional advantage for blowers used in NIVV devices.

In an embodiment, at least some of the components of the stationary portion may be made from aluminum, or an alloy thereof, e.g., aluminum die castings. In another embodiment, at least some of the components of the stationary portion may be made from magnesium, or an alloy thereof. In yet another embodiment, at least some of the components of the stationary portion may be made from a plastic material.

3.2 Inlet

The air inlet 130 is adapted to allow sufficient airflow into the blower to ensure desired flow requirements are met while not allowing excessive noise emission back out of the air inlet 130. Also, the dimensions of the air inlet 130 are dependent upon the desired level of flow required by the blower and the particular application of use. In a NIVV embodiment, the air inlet 130 may have a diameter between 2 mm and 100 mm, e.g., between 15 mm and 20 mm.

3.3 Stator Components

The stator components including stator vanes are structured to promote a smooth transition in flow direction. In an embodiment, two of the stator components 180, 182 are injection molded from a plastic (e.g., see FIGS. 7a-7d). The third stator component includes stator vanes 184 molded into the bottom casing 174. In another embodiment, the stator vanes may be made using a thermally conductive material such as metal.

3.3.1 Radial Flow Direction

In an NIVV embodiment of the invention, the stator vanes direct flow in a generally radial direction. The vanes have a height in the range of 1 mm to 100 mm, e.g., 3 mm to 5 mm. This arrangement brings the flow through an approximate right angle and assists in maintaining a compact design for the blower as a whole when compared to vanes or stage-to-stage paths that include a significant axial component.

3.3.2 Shape

Each stage has a plurality of stator vanes to direct the airflow, e.g., between 2 and 100 stator vanes. In one embodiment, each stage has 7 stator vanes. Each vane is substantially identical and has a generally spiral shape with a radius of curvature that is smaller at its inner end than at its outer end, to decelerate the air before turning it too hard.

In other applications, such as ones where very high flow rates are needed and noise is not a main consideration, the air may not be decelerated by the stator vanes.

3.3.3 Mixed Axial/Radial Flow Direction

Figure 10A:
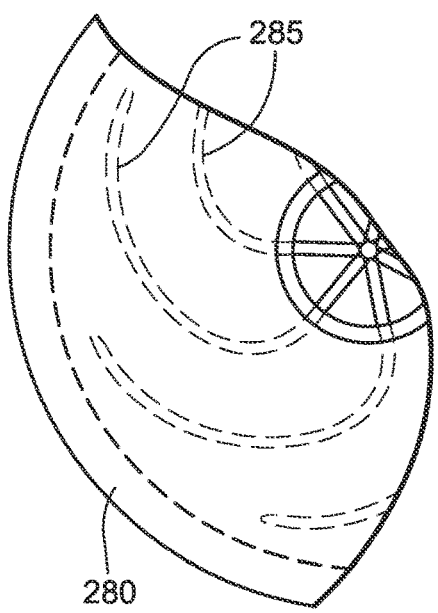
FIGS. 10a to 10b show various views of an alternative stator component according to an alternative embodiment of the invention.
Figure 10B:
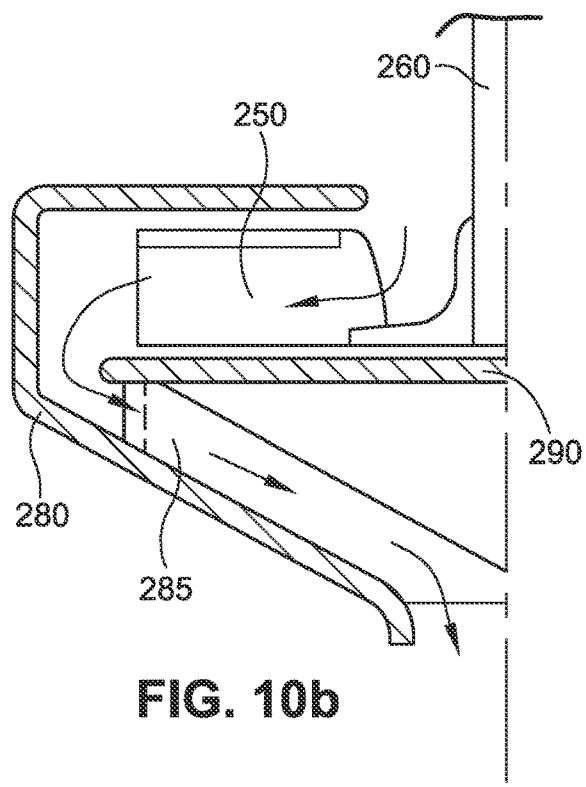
Figure 11:
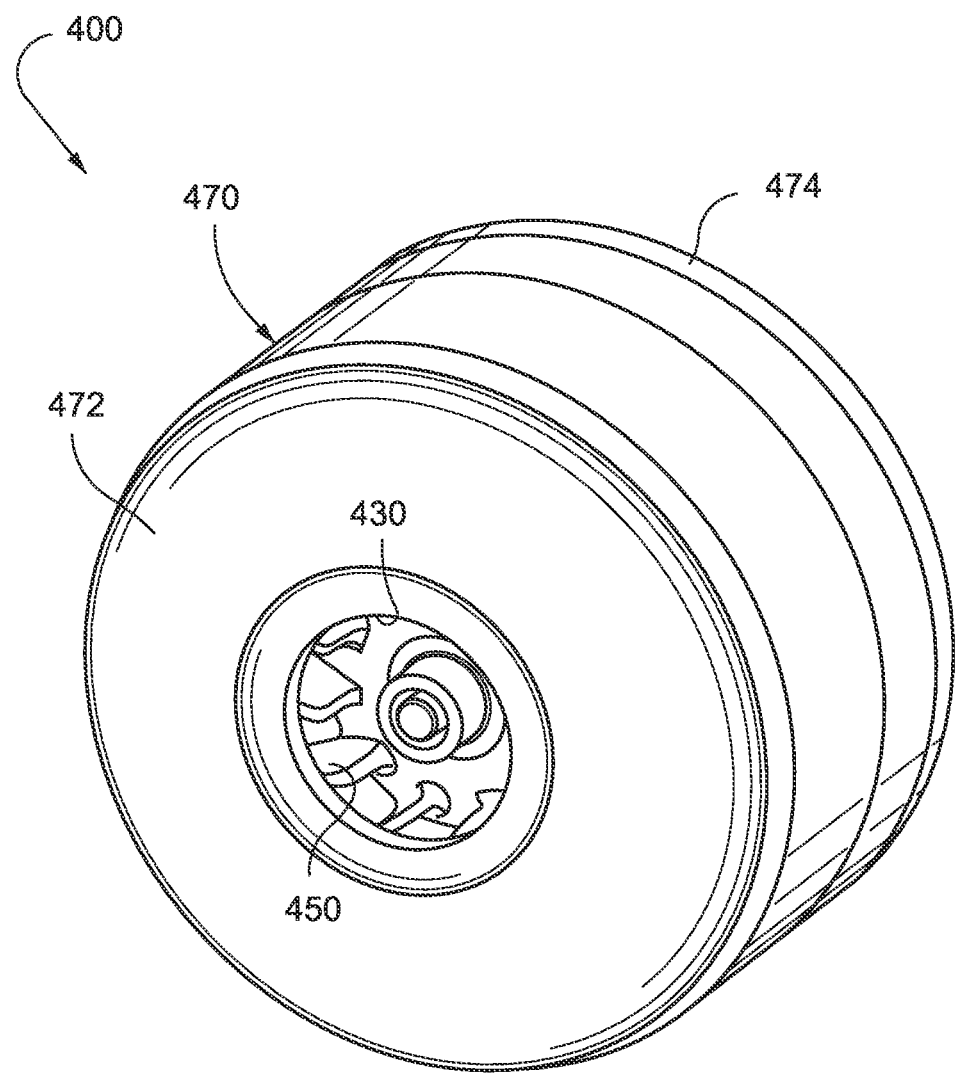
FIGS. 11-14 show various views of a blower according to another embodiment of the present invention.

In an alternative embodiment of the invention, the vanes may direct flow in a plane normal to the axis, or there may be an axial component to the directed flow such that at least one set of stator vanes direct flow in both radial and axial directions. In such an embodiment, the stator vanes on the final stage can be positioned on an incline or otherwise are not of constant height, but develop axially as well as radially, such that the air is turned more gradually to the axial direction. For example, FIGS. 10a and 10b illustrate impeller 250 attached to motor shaft 260, a shield 290, and a stator 280 including stator vanes 285 structured to direct flow in both radial and axial directions. Thus, the vanes begin tangentially (as they do in the above embodiments), but end up directing the flow axially (rather than radially as in the above embodiments). This arrangement may improve pressure generation, though it takes up a little more space. This arrangement means that air does not pass through a right angle.

3.4 Shield Isolating Stator Vanes

Figure 8A:
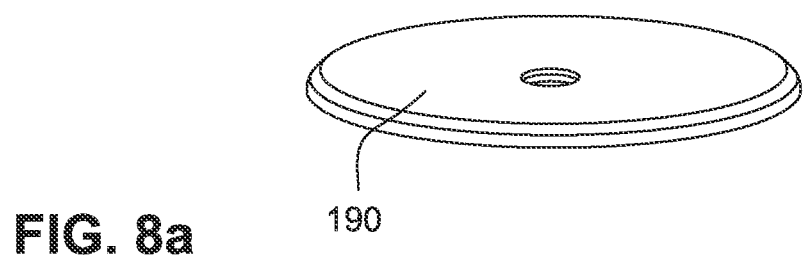
FIGS. 8a to 8c show various views of a shield according to an embodiment of the invention.
Figure 8B:
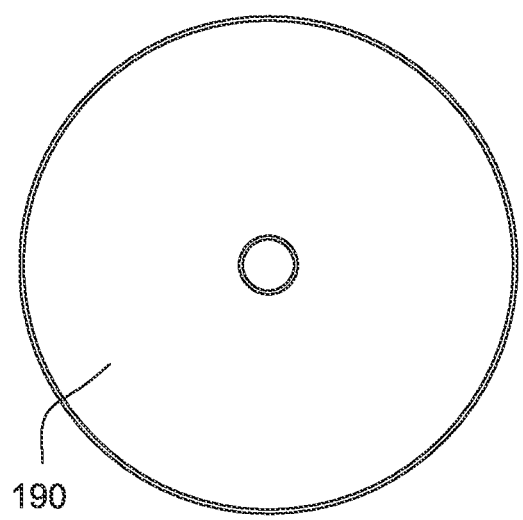
Figure 8C:
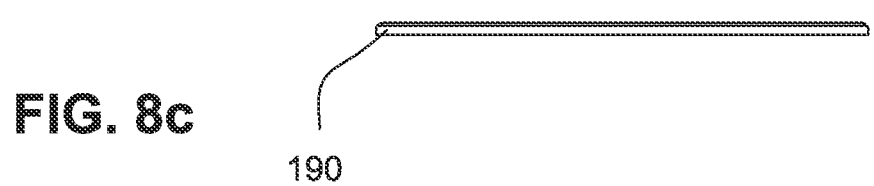

Another aspect of the invention relates to a shield, located between stator vanes and impeller blades (e.g., see FIGS. 8a-8c). In an embodiment, the shield is formed of injection molded plastic although other suitable materials (such as metals) may be used. In the illustrated embodiment, the shield extends radially beyond the outer edge of the stator vanes. This means there is not a "line-of-sight" path between the stator vanes and impeller blades and consequently acts to ensure that the airflow impinging on the stator blades is of a uniform circulating nature.

Figure 5A:
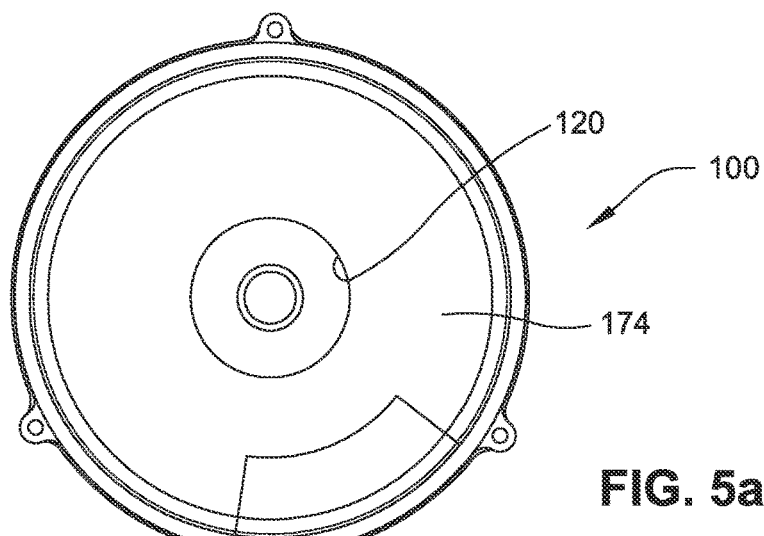
FIGS. 5a to 5g show various views of the blower shown in FIGS. 3a-3g.
Figure 5B:
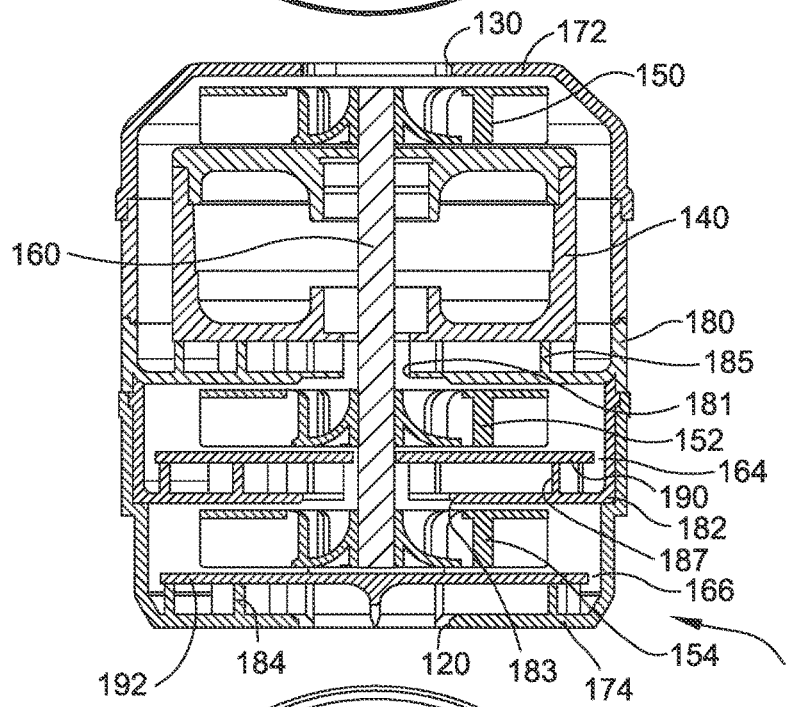
Figure 5C:
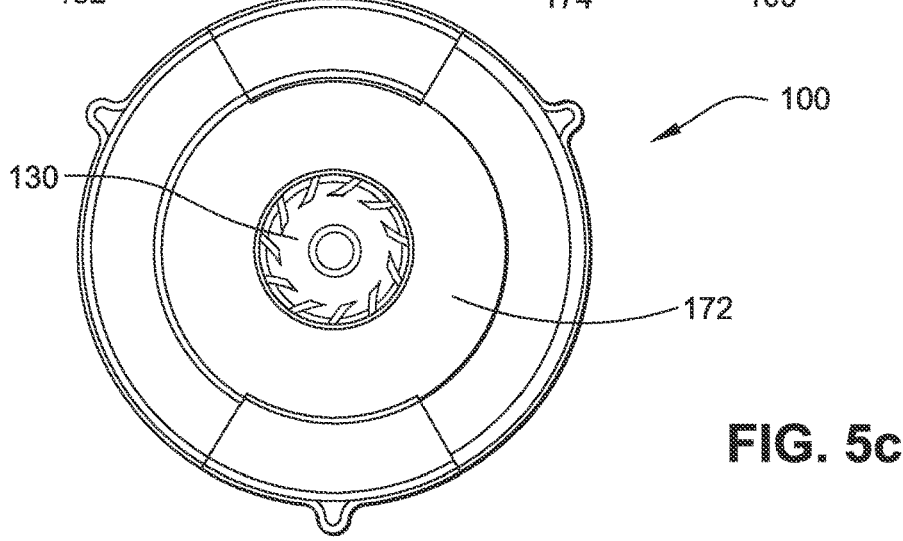
Figure 5D:
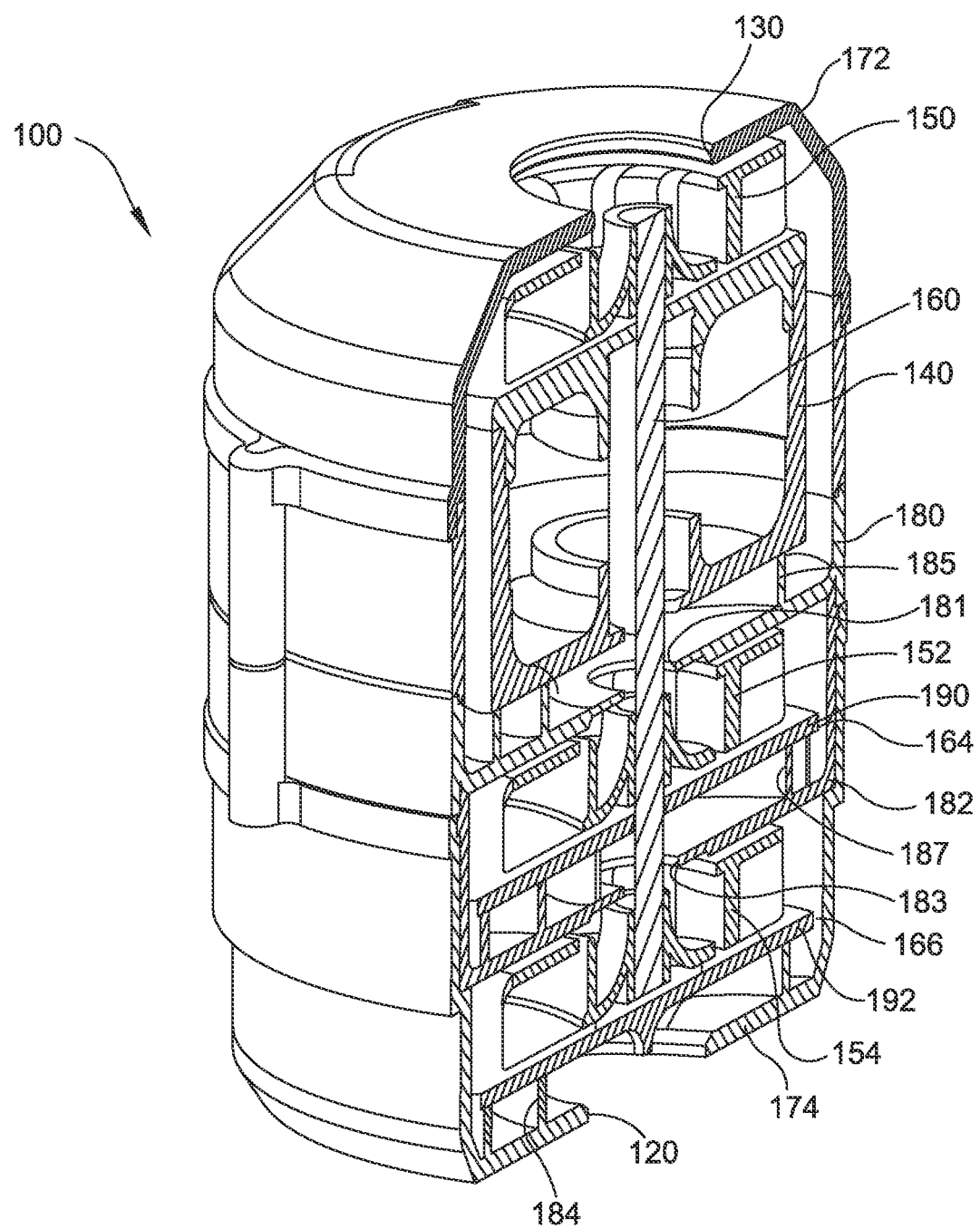
Figure 5E:
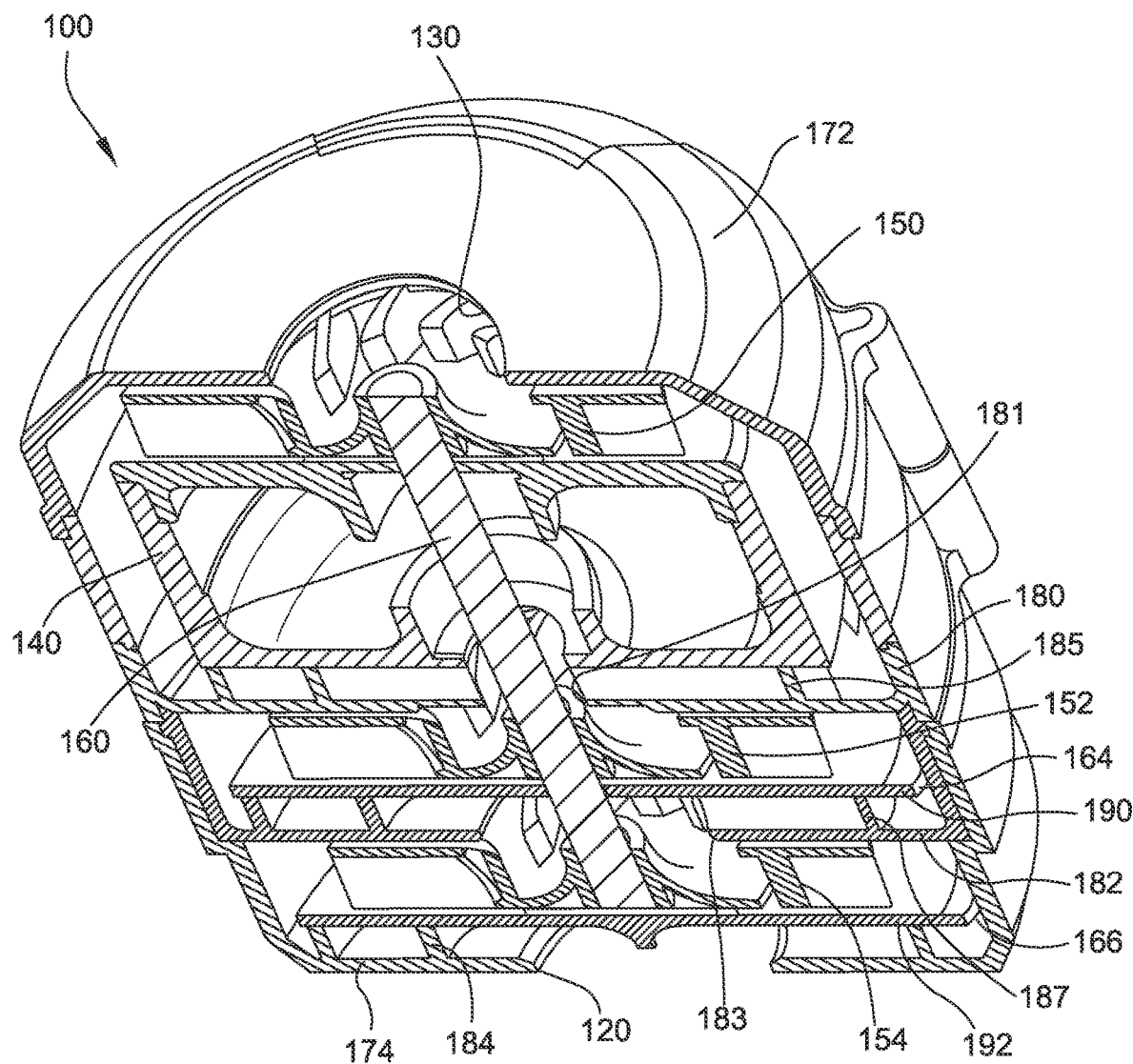
Figure 5F:
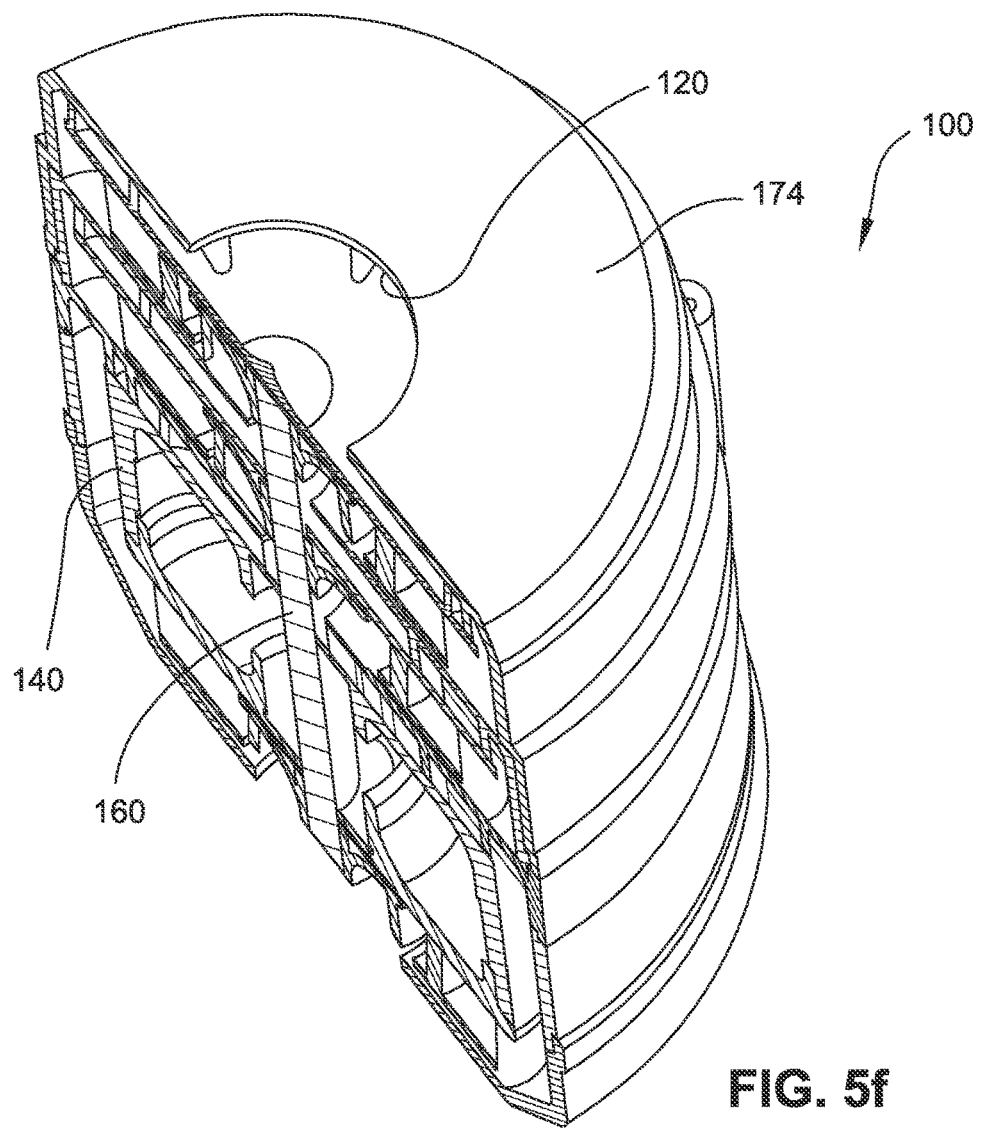
Figure 5G:
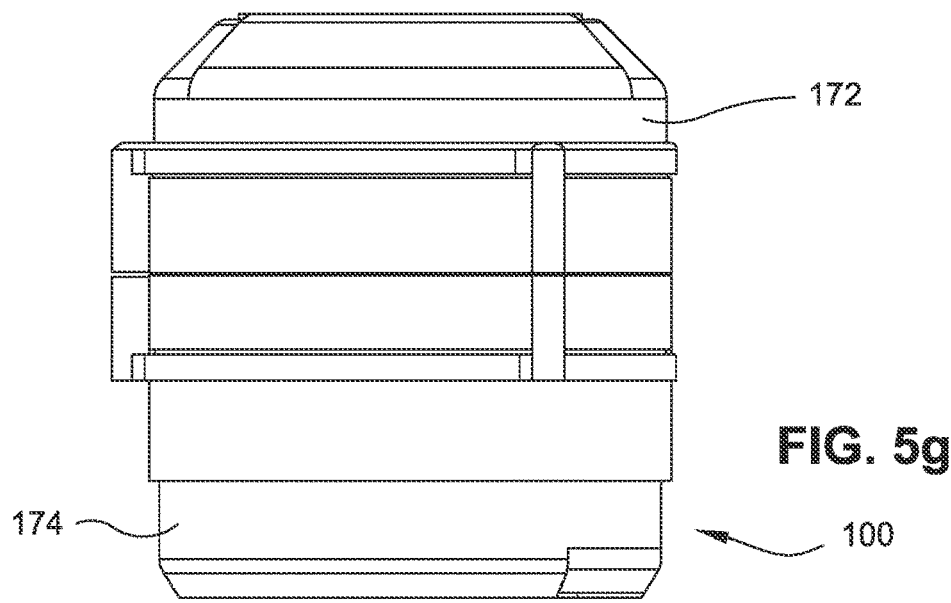
Figure 6A:
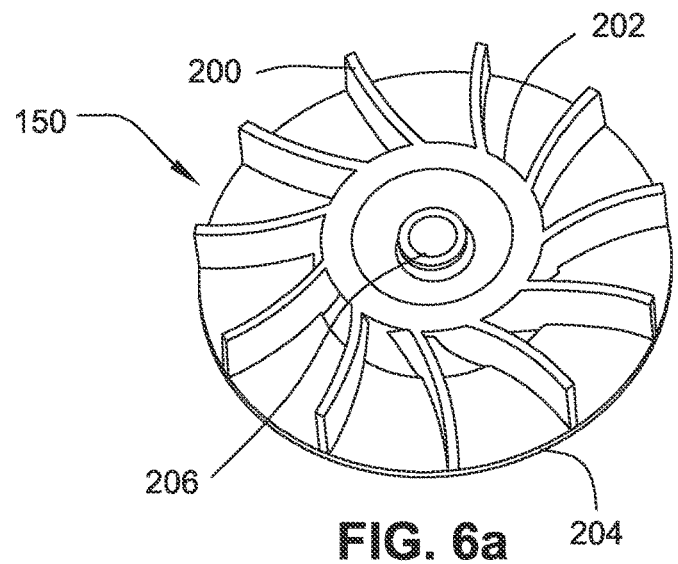
Figure 6B:
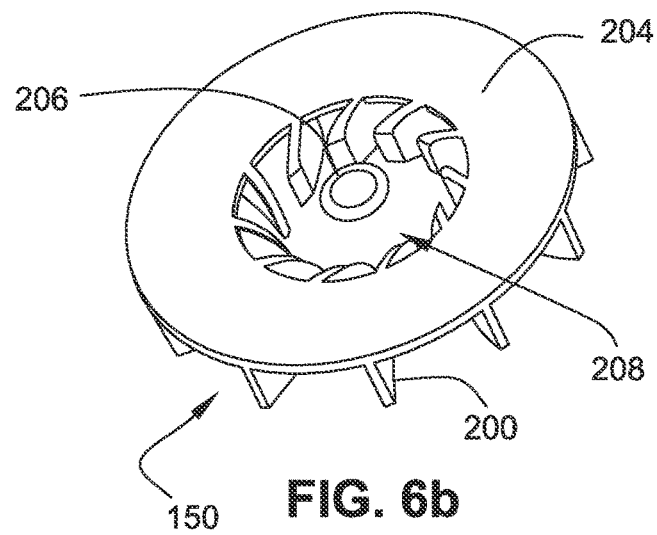
Figure 6C:
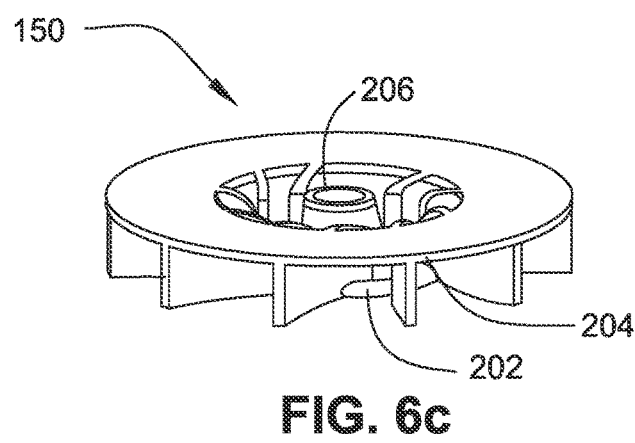

As best shown in FIGS. 5b, 5d, and 5e, shield 190, 192 directs the flow via an annular aperture 164, 166, respectively. A peripheral aperture may also be used. In one form, the shield leaves only a narrow annular gap between its outer edge and the wall of the stationary portion. The gap is sufficient to allow enough airflow to the next stage without introducing excessive pressure drop. In an embodiment for a blower for use in a NIVV device, the gap may be between 0.5 mm and 100 mm, e.g., between 1 mm and 2 mm. The shield also provides an acoustic barrier by isolating the impeller blade pressure pulses from the stator vanes.

In one form, the shield is a circular disc and in NIVV devices may be welded to the stator vanes.

Figure 9:
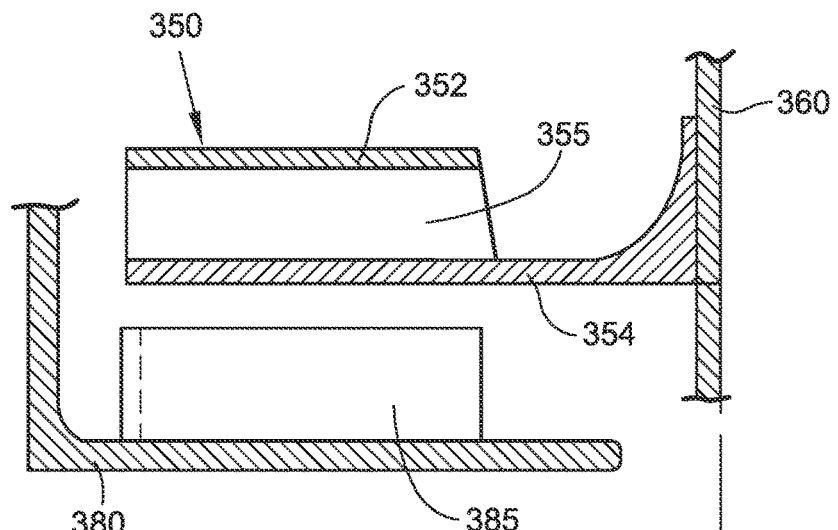
FIG. 9 shows a two-shrouded impeller according to an alternative embodiment of the invention.

In an alternative embodiment, the shield may rotate. Such a rotating shield may be integral to the impeller such that the lower shroud acts as a rotating shield between the impeller blades and stator vanes. For example, FIG. 9 illustrates impeller 350 attached to motor shaft 360. The impeller 350 includes upper and lower shrouds 352, 354 with the lower shroud 354 acting as a rotating shroud between impeller blades 355 and stator vanes 385 of stator 380.

3.5 Outlet

In contrast to the known prior art centrifugal blowers which direct air exiting the blower in a generally tangential direction, a centrifugal blower in accordance with an embodiment of the present invention directs air in a generally axial direction. This axis-symmetry is effective in reducing airflow turbulence and in reducing blade pass tone, as the impeller and vanes experience symmetrical flow patterns at all device flow rates.

3.6 Housing

The housing comprises chamfers on the external housing to assist with fitting the separate components of housing together. This design allows for an overall smaller package.

A gap between the interior wall of the external housing and the external wall of motor allows air to pass down around the sides of the motor. In an embodiment, the size of the gap is sufficient to prevent significant frictional losses but not too large that the overall size of the device becomes excessive. In an embodiment for a blower used in NIVV devices, the size of the gap may be between 0.1 mm and 100 mm, e.g., approximately 4 mm.

The ability of the air to flow around the motor may assist in keeping the motor cool. It may also assist in heating the patient air in an NIVV device.

4. Rotating Portion

4.1 Impeller

Figure 4B:
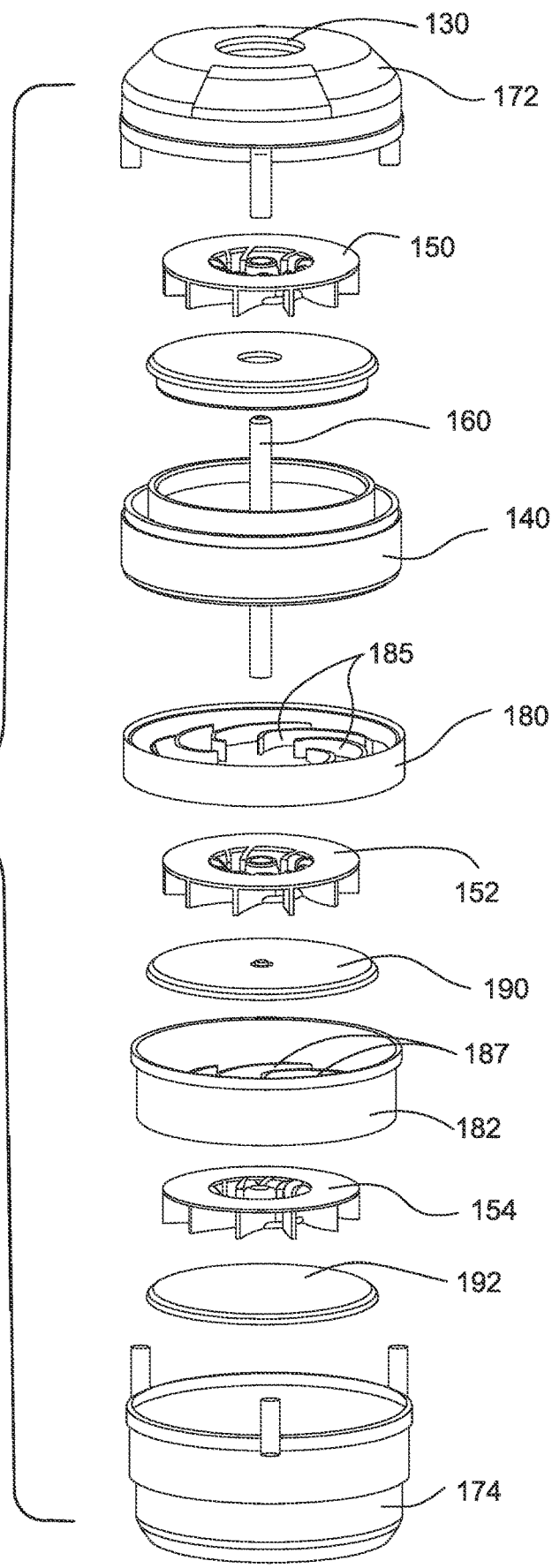
Figure 4C:
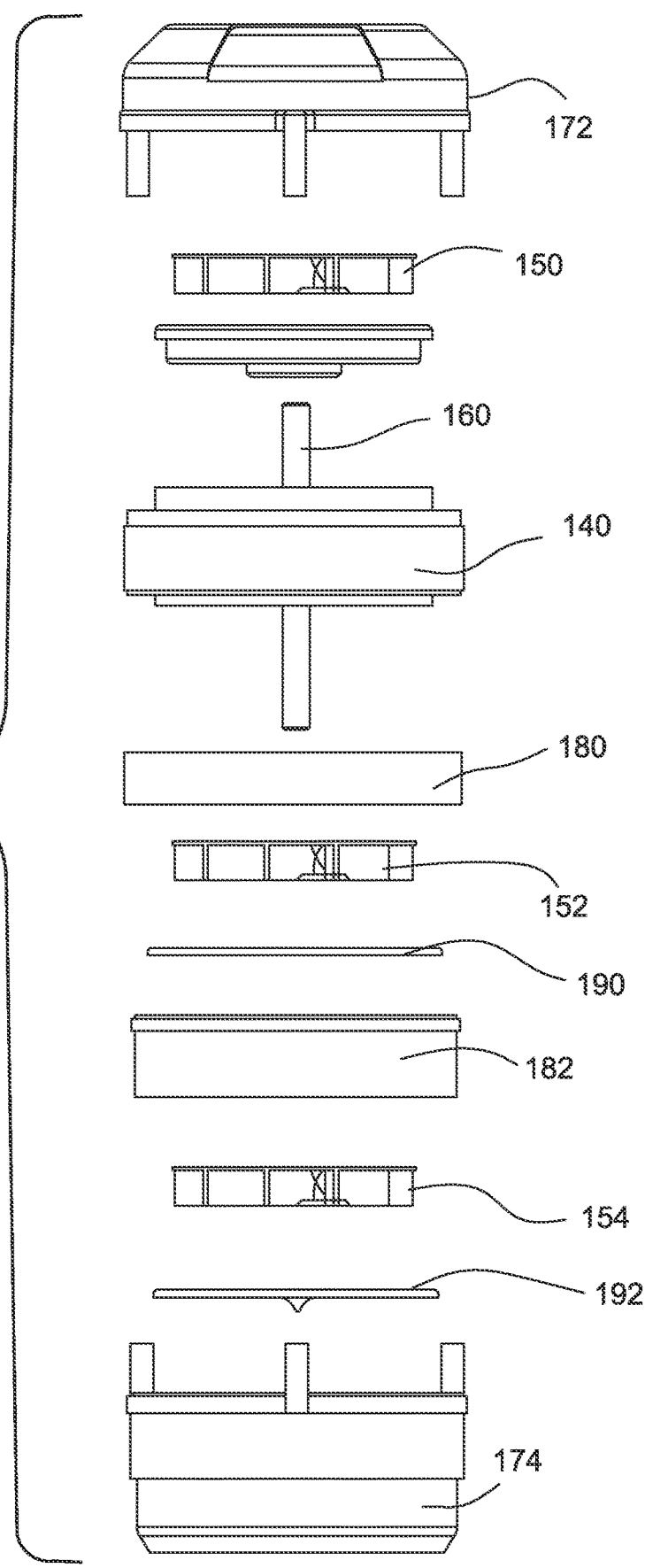

In an NIVV embodiment, a blower comprises a plurality of impellers 150, 152, 154 as shown in FIGS. 4a to 4c. In the illustrated embodiment, the impellers are identical in design, thus only impeller 150 will be described in detail. With particular reference to FIGS. 6a to 6g, impeller 150 is of one-piece molded plastic construction, although other suitable materials and manufacturing techniques could be employed. The impeller 150 comprises a plurality of continuously curved blades 200 sandwiched between a pair of disk-like shrouds 202, 204. The smaller shroud 202 incorporates the hub or bushing 206 that is adapted to receive the motor shaft 160. The shroud 202 overlaps an inner portion of the blades 200, i.e., the outer diameter (OD) of the smaller shroud is substantially smaller than the OD of the larger shroud 204. The larger shroud 204 is formed with a relatively large center opening 208 and extends to the radially outer tips of the blades. Making the OD of the smaller shroud 202 slightly smaller than the diameter of the center opening 208 in shroud 204 facilitates the molding process used to manufacture the impellers.

By utilizing differentially sized shrouds, the inertia of the impeller 150 is reduced while the overall rigidity of the impeller is maintained. In this regard, the impeller 150 may be constructed of a polycarbonate, polypropylene, polyamide, or other material which provides acoustic dampening properties that dampen the resonance of the impellers. Glass fiber reinforcement may be employed to increase the stiffness of any of these materials.

4.1.1 Diameter

In an NIVV embodiment, the impeller 150 may have a diameter in the range of 20 mm to 200 mm. In one embodiment, the impeller 150 may have a diameter in the range of 40 mm to 50 mm, for example 42 mm. An impeller with a diameter in this range may provide a good compromise between overall size of the blower, rotational inertia, and turbulence levels.

4.1.2 Number of Blades

In an NIVV embodiment, the impeller has 4-100 primary blades 200, e.g., 11. The impeller may include secondary and tertiary blades and may be of variable blade passage cross section (not shown).

4.1.3 Blade Shape

In an embodiment, the impeller blades 200 are continuously curved in radial direction, and may also be tapered in width in the radially outer portions. The reduced width at the tips of the blades may reduce turbulence (e.g., Reynolds number is less in blowers with 3 impellers, 2 impellers, 1 impeller (in order)). In one embodiment, the outermost transverse edges of the blades may be stepped along their respective transverse widths (not shown) to assist in reducing turbulence noise at the tips of the blades. In another embodiment, the outermost transverse edges of the blades 200 are flat. In an embodiment, the blades 200 have an outlet height in the range of 1 mm to 40 mm, e.g., 3 to 6 mm. In one form, the blades 200 have an inlet height that is the same as the outlet height, however in other forms, the inlet and outlet heights may be different.

The blades 200 have an inlet angle with respect to a tangent of between 0° and 90°, e.g., about 20°. The blades have an outlet angle with respect to a tangent between 70° and 110°, however other angles are possible.

4.2 Shaft

In an embodiment, there is a gap between the shaft 160 and the shields 190, 192. This gap is sufficient to allow the shaft to rotate within the shields but is small enough to prevent significant leak between the impellers 152, 154 and the internal flow directing components 182, 184. In a blower for a NIVV device, the gap may be less than 10 mm, e.g., less than 2 mm.

5. Axial Symmetry

The blower according to an embodiment of the present invention comprises axially symmetric volutes, using stator vanes. The airflow enters and exits each stage within the blower in a substantially axial direction. Consequently, the air enters the blower axially at one end, and leaves it axially at the other. The airflow path is substantially axially symmetrical throughout the blower maintaining a constant feed pattern through the impeller, and in the volute. The symmetric blower provides balance, which leads to lower levels of blade pass tone, and lower levels of turbulence noise. Shields positioned between the impeller and the stator vanes provide a barrier for the vane leading edges from the impeller blade tips, thus reducing blade pass tone.

6. Multiple Stages

In the illustrated embodiment, the blower includes three stages with three corresponding impellers. In this embodiment, one impeller is positioned on one side of the motor and two impellers on the other side of the motor.

In an alternative embodiment, the blower may include two stages, one on either side of the motor. Another further embodiment uses four stages, with two on either side of the motor. Another embodiment is a single stage design. A further embodiment comprises multiple stages only on one side of the motor.

7. Alternative Embodiments

The following illustrates blowers according to alternative embodiments of the present invention. In each embodiment, air enters the blower axially at one end, and leaves the blower axially at the other end.

7.1 Two-Stage Blower

FIGS. 11-16 illustrate a blower 400 according to another embodiment of the present invention. As illustrated, the blower 400 includes two stages with two corresponding impellers 450, 452. In this embodiment, the two impellers are positioned on the same side of the magnet 462 and the stator assembly 465 but a bearing 444 is positioned between the impellers 450, 452.

Such blower may be used in Snore PAP, CPAP, APAP, and/or VPAP and may be configured to provide a ventilator variant.

7.1.1 Compact Size

Figure 14:
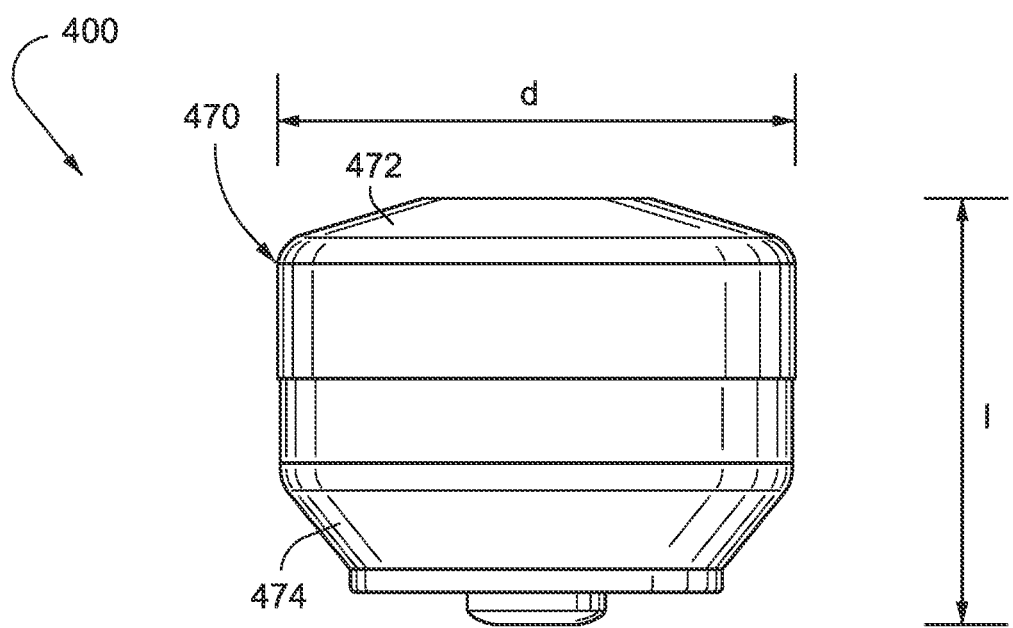

The blower 400 has a relatively tiny size to provide a more compact or miniature blower. For example, as shown in FIG. 14, the blower 400 may have an overall diameter d of about 50-60 mm, e.g., 53 mm, and an overall length 1 of about 40-50 mm, e.g., 44 mm. However, other suitable sizes are possible.

7.1.2 General Description

The stationary portion of the blower 400 includes a housing 470 with first and second housing parts 472, 474, a stator component 480 including stator vanes 485, and first and second shields 490, 492. The rotating portion of the blower 400 includes first and second impellers 450, 452 adapted to be driven by motor 440. The motor includes a magnet 462 provided to shaft 460 and a stator assembly 465 to cause spinning movement of the shaft 460. In an embodiment, the motor may include 2 poles (for compact size), be sensorless, and/or be slotless (for low noise).

Figure 12:
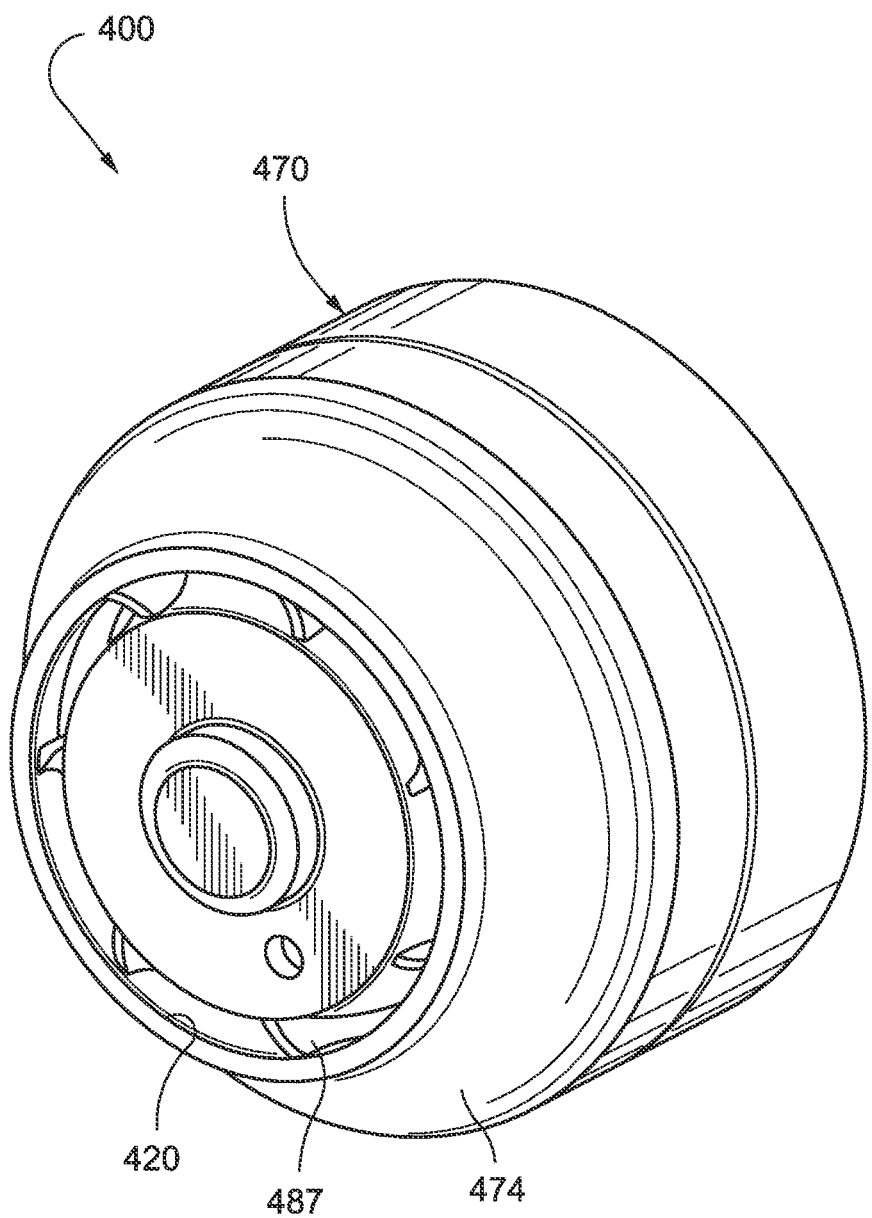
Figure 13:
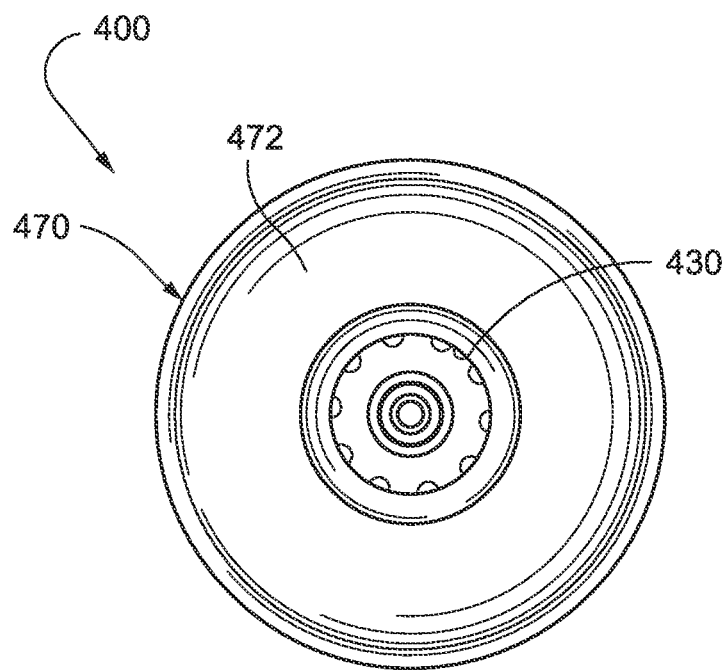
Figure 16:
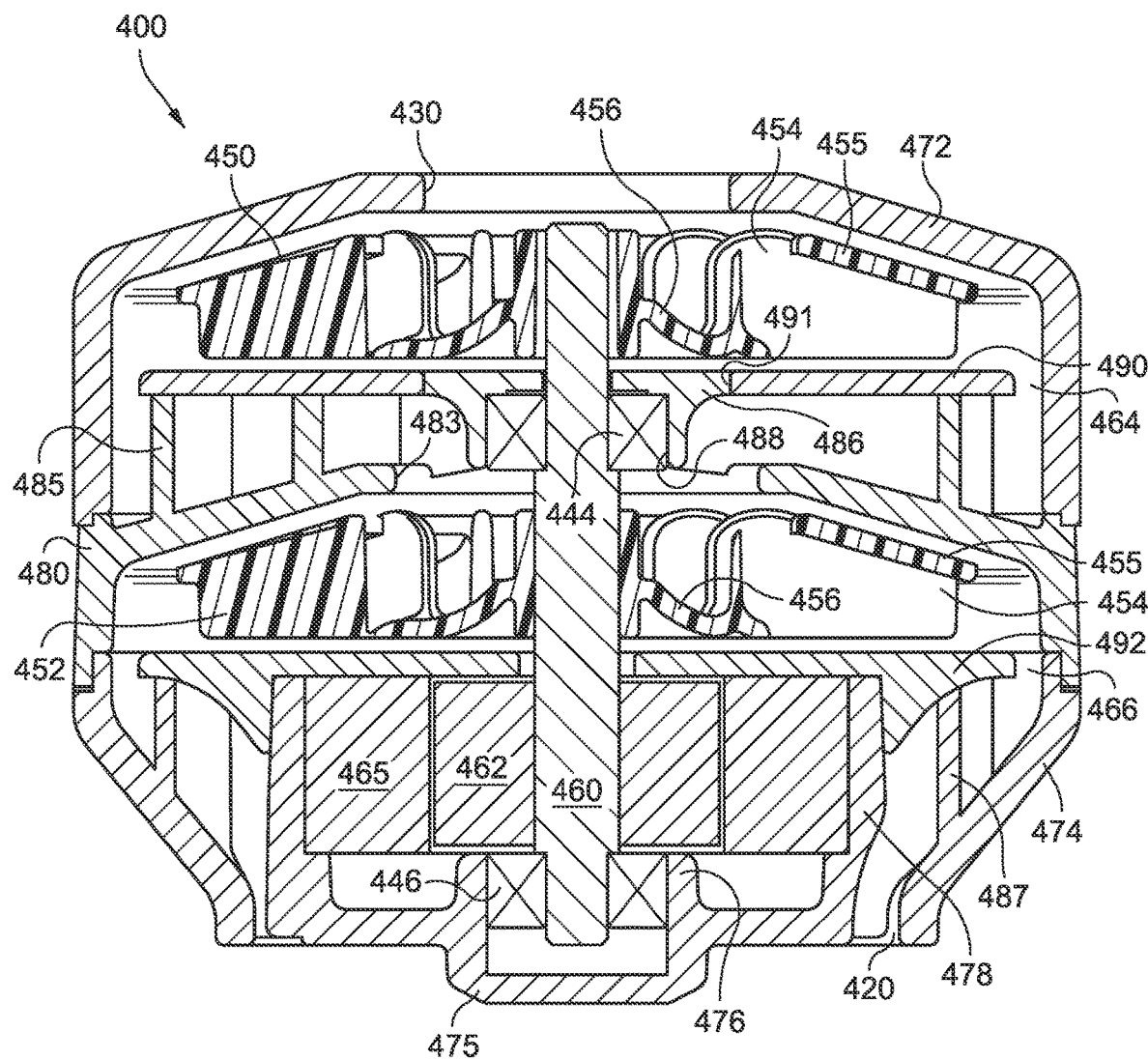
FIG. 16 is a cross-section view of the blower shown in FIGS. 11-14.

The blower 400 is generally cylindrical and has an inlet 430 provided by the first housing part 472 at one end and an outlet 420 provided by the second housing part 474 at the other end. As best shown in FIGS. 12 and 16, the outlet 420 has an annulus or ring shape. In an embodiment, the inlet may also have an annulus or ring shape (not shown).

Similar to the above embodiments, the blower 400 has axial symmetry and air enters the blower axially at one end and leaves the blower axially at the other end. Such arrangement may provide relatively low noise in use, e.g., due to axial symmetry and/or low volute turbulence.

7.1.3 Stationary Portion

Figure 15:
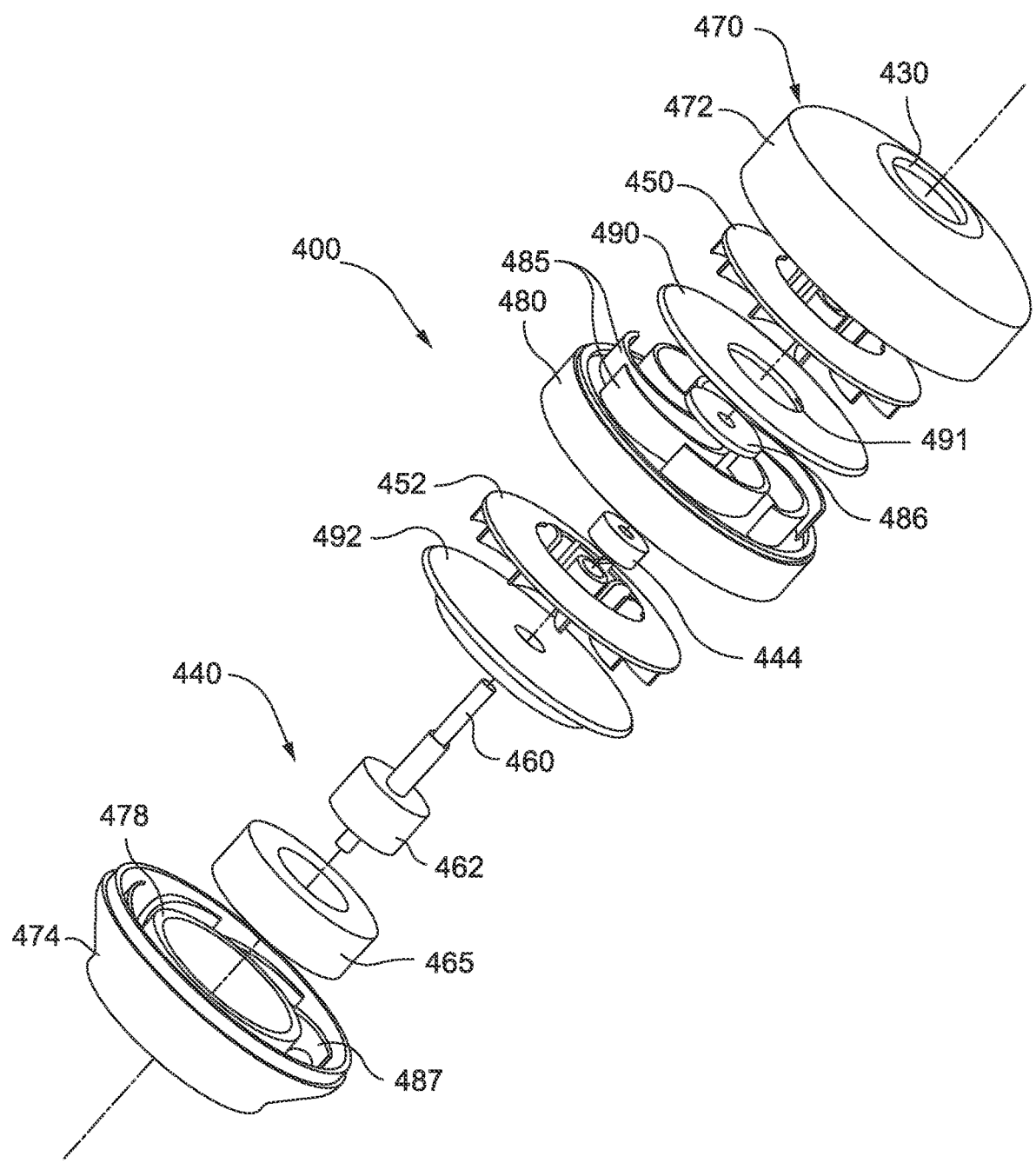
FIG. 15 is an exploded view of the blower shown in FIGS. 11-14.

As best shown in FIGS. 15 and 16, the stator component 480 includes a cylindrical hub 486 that engages within a corresponding opening 491 provided to the shield 490, e.g., press-fit, to secure the shield 490 in position. In addition, the hub 486 provides a recess 488 to retain or house a bearing 444 that rotatably supports the shaft 460. As illustrated, the bearing 444 is recessed into the stator component 480 so that it is positioned along a plane of where air is fed from the impeller 450. This arrangement saves space axially because the bearing 444 is positioned out of the housing that encloses the motor component, i.e., stator assembly and magnet.

As best shown in FIGS. 15 and 16, the housing part 474 includes stator vanes 487 to direct flow towards the outlet 420. In addition, the housing part 474 includes an outer annular flange 478 and a hub 475 that provides an inner annular flange 476 to support motor components. Specifically, the inner annular flange 476 retains or houses a bearing 446 that rotatably supports the shaft 460. The outer annular flange 478 retains or housings the stator assembly 465. The shield 492 engages the outer annular flange 478, e.g., press-fit, to enclose the stator assembly 465 along with the magnet 462 on the shaft 460 within the housing part 474.

In an embodiment, the housing part 474 may be constructed of metal so that the housing part 474 can act as a heat sink to conduct and dissipate heat generated from the stator assembly 465 in use. Also, at least a portion of the outer annular flange 478 supporting the stator assembly 465 is exposed to the flow of air, which allows cooling of the stator assembly 465 as air flows through the housing part 474 in use. However, the housing part along with other blower components may be constructed of other suitable materials, e.g., aluminum, plastic, etc.

7.1.4 Rotating Portion

In the illustrated embodiment, each impeller 450, 452 includes a plurality of continuously curved or straight blades 454 sandwiched between a pair of disk-like shrouds 455, 456. The lower shroud 456 incorporates the hub or bushing that is adapted to receive the shaft 460. Also, each impeller 450, 452 includes a tapered configuration wherein the blades 454 taper towards the outer edge. Further details of impellers are disclosed in PCT Application No. PCT/AU2006/001617, filed Oct. 27, 2006, which is incorporated herein by reference in its entirety. Such arrangement may provide relatively fast pressure response, e.g., due to relatively low inertia impellers.

7.1.5 Fluid Flow Path

In the first stage, air or gas enters the blower 400 at the inlet 430 and passes into the first impeller 450 where it is accelerated tangentially and directed radially outward. Air then flows in a spiral manner with a large tangential velocity component and also an axial component passing through the gap 464 defined by the outer edge of the shield 490 and the inner surface of the housing part 472. Air then enters the stator vanes 485 formed in the stator component 480 and is directed radially inwardly towards orifice 483, and thereafter onto the second stage.

In the second stage, air or gas passes into the second impeller 452 where it is accelerated tangentially and directed radially outward. Air then flows in a spiral manner with a large tangential velocity component and also an axial component passing through the gap 466 defined by the outer edge of the shield 492 and the inner surface of the housing part 474. Air then enters the stator vanes 487 formed in the housing part 474 and is directed towards the outlet 420.

7.1.6 Support System

Figure 17:
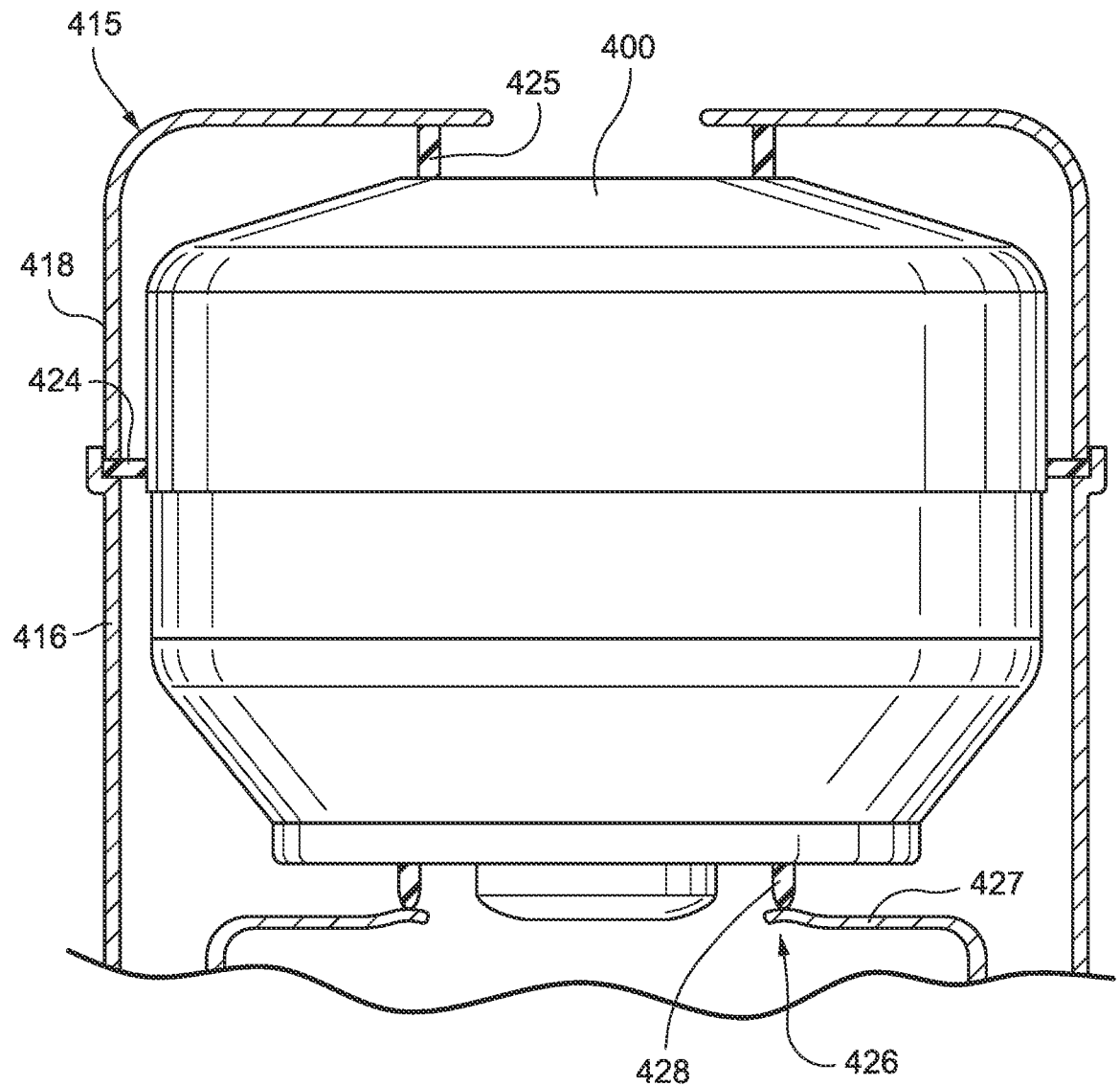
FIG. 17 is a cross-sectional view illustrating a support system for a blower according to an embodiment of the present invention.

As shown in FIG. 17, the blower 400 may be supported within an outer casing 415 (e.g., forming a portion of a NIVV device such as a PAP device) by a support system. The outer casing 415 includes a base 416 and a cover 418 provided to the base 416. The support system includes a side support 424, a top support 425, or a bottom support 426 or combinations thereof to support the blower 400. The support system may also be adapted to provide a seal between the inlet and the outlet sides of the blower 400.

The side support 424 may be in the form of an annular flexible ring adapted to support the blower in a flexible and/or vibration-isolated manner within the outer casing 425. In addition, the flexible ring 424 divides the inlet of the outer casing 425 from the outlet of the outer casing 425 to avoid the need for a connection tube that directs flow towards the outlet of the outer casing. Also, the flexible ring 424 may provide a seal between the base 416 and the cover 418 of the outer casing 415.

The bottom support 426 includes a biasing member 427, e.g., leaf spring, and a conducting member 428. In use, the bottom support 426 provides a flexible structure to isolate the blower 400 from the outer casing 415, e.g., vibration isolated. In an embodiment, the conducting member 428 is coupled with the stator assembly 465 to conduct current from an external source to the stator assembly 465.

7.2 Two-Stage Blower with Bearing Tube

Figure 18:
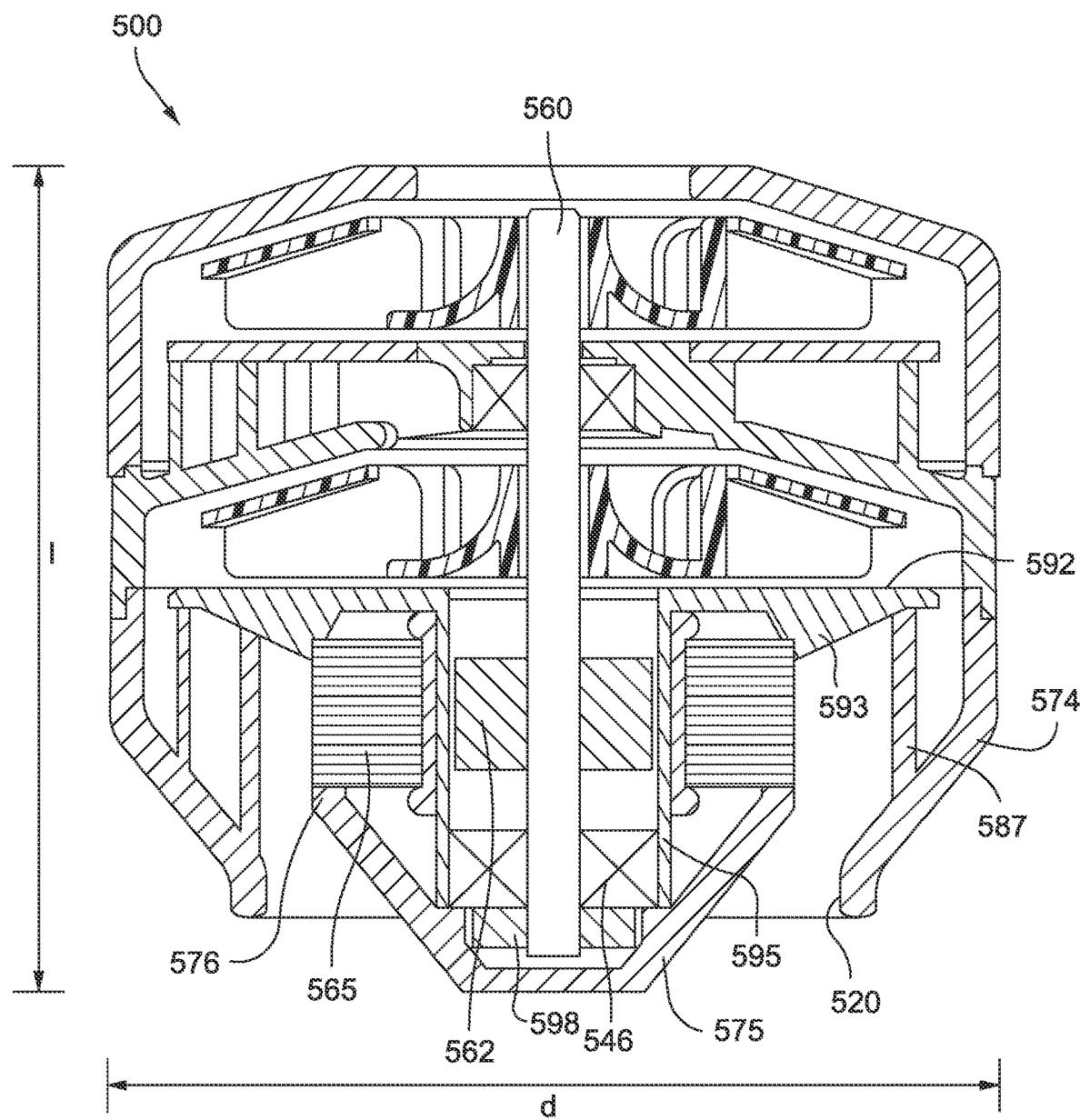
FIG. 18 is a cross-sectional view of a blower according to another embodiment of the present invention.

FIG. 18 illustrates a two-stage blower 500 according to another embodiment of the present invention. The two-stage blower 500 is similar to blower 400 described above. In contrast, the second housing part 574 and second shield 592 provide a different structure for supporting motor components.

As illustrated, the second housing part 574 includes stator vanes 587 to direct flow towards the outlet 520. In addition, the housing part 574 includes a hub 575 that provides an annular flange 576. The annular flange 576 is structured to engage a lower side of the stator assembly 565.

The second shield 592 includes a tube portion 595 extending therefrom (e.g., integrally formed in one piece). As illustrated, the stator assembly 565 is provided along an exterior surface of the tube portion 595 such that the stator assembly 565 is enclosed and sandwiched between the annular flange 576 of the second housing part 574 and a tapered projection 593 on the shield 592.

In the illustrated embodiment, the exterior surface of the stator assembly 565 is exposed to the flow of gas passing through the housing part 574, which allows cooling of the stator assembly 565 in use. Also, heat from the stator assembly may be used to heat the gas for the patient without the need for a separate heater.

The interior surface of the tube portion 595 retains or houses a bearing 546 that rotatably supports the shaft 560. In addition, the tube portion 595 encloses the magnet 562 on the shaft 560, which is aligned with the stator assembly 565. In an embodiment, the tube portion 595 may be "magnetically transparent", which allows the stator assembly 565 to act on the magnet 562 positioned within the tube portion 595 without significant loss of flux density and/or increased heat, if any. Further details of a magnetically transparent tube are disclosed in U.S. Provisional Application No. 60/853,778, filed Oct. 24, 2006, which is incorporated herein by reference in its entirety.

A balance ring 598 may be optionally provided to an end portion of the shaft 560 (e.g., opposite the end portion supporting the impellers).

In the illustrated embodiment, the hub 575 protrudes further outwardly from the housing than the hub 475 of the blower 400 described above. This arrangement may add about 1-10 mm, e.g., 5 mm, to the height of the blower 500, e.g., with respect to the blower 400. For example, the blower 500 may have an overall diameter d of about 50-60 mm, e.g., 53 mm, and an overall length 1 of about 40-55 mm, e.g., 49 mm. However, other suitable sizes are possible.

7.3 Three-Stage Blower with Tapered Configuration

Figure 19:
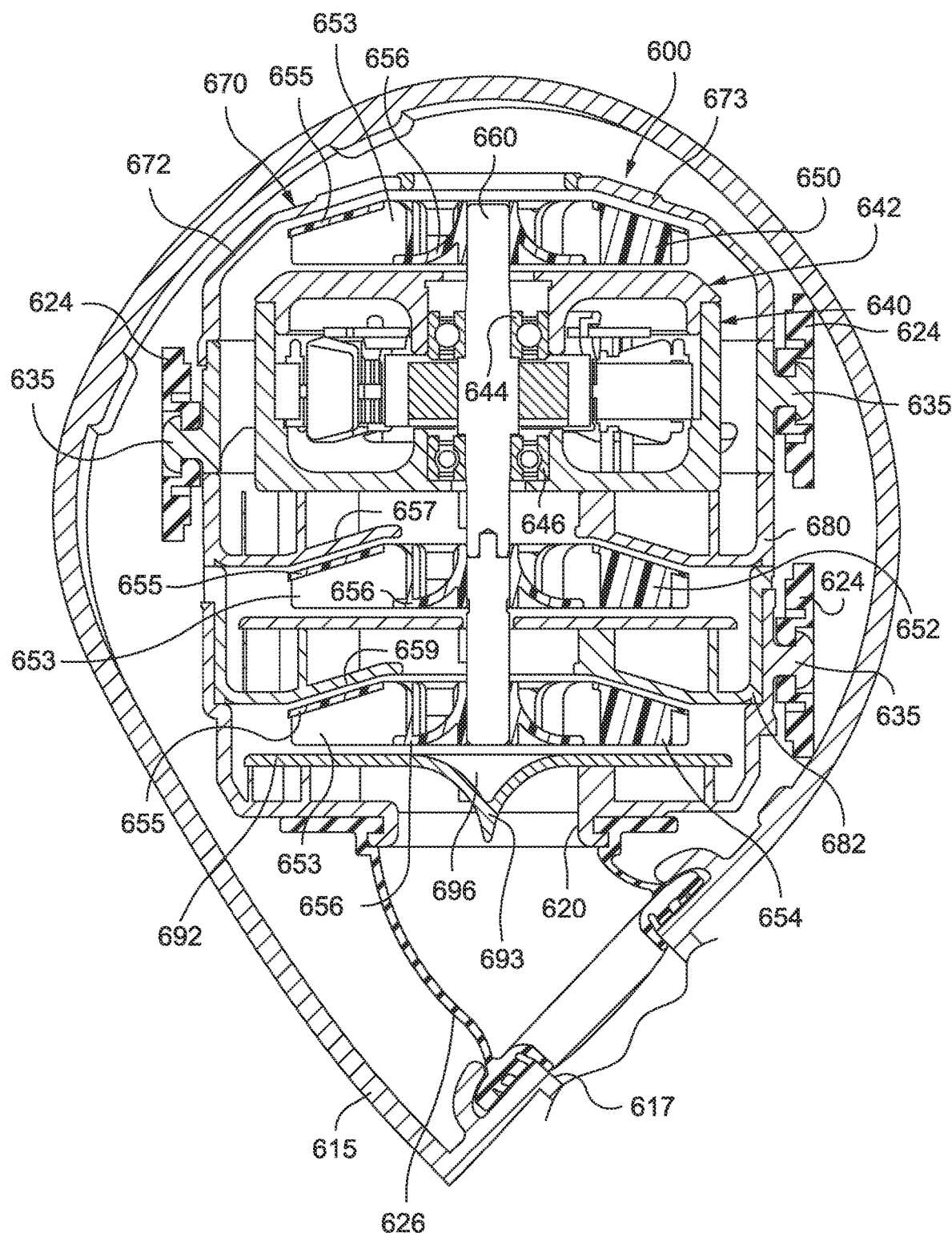
FIG. 19 is a cross-sectional view of a blower according to another embodiment of the present invention.

FIG. 19 illustrates a three-stage blower 600 according to another embodiment of the present invention. Similar to the three-stage blower 100 described above, the blower 600 includes three stages with one impeller 650 positioned on one side of the motor 640 and two impellers 652, 654 positioned on the other side of the motor 640.

In the illustrated embodiment, each impeller 650, 652, 654 of the blower 600 has a tapered configuration. In addition, corresponding portions of the housing 670 and stator components 680, 682 are tapered to match the tapered configuration of the impellers 650, 652, 654.

In the illustrated embodiment, each impeller 650, 652, 654 includes a plurality of continuously curved or straight blades 653 sandwiched between a pair of disk-like shrouds 655, 656. The lower shroud 656 incorporates the hub or bushing that is adapted to receive the shaft 660. Also, each impeller 650, 652, 654 includes a tapered configuration wherein the blades 653 taper towards the outer edge. Further details of impellers are disclosed in PCT Application No. PCT/AU2006/001617, filed Oct. 27, 2006, which is incorporated herein by reference in its entirety.

The upper wall 673 of the housing part 672 is tapered to match the tapered configuration of impeller 650, and the lower wall 657, 659 of respective stator components 680, 682 are tapered to match the tapered configuration of impellers 652, 654.

Also, in the illustrated embodiment, a central portion 693 of the lower shield 692 is shaped to direct the airflow down towards the outlet 620. The central portion 693 includes a void 696 along the surface facing the impeller 654, e.g., to maintain a constant section/thickness for the shield 692 and save on material costs.

As illustrated, the bearings 644, 646 that support the shaft 660 are provided within the housing 642 of the motor 640. In an alternative embodiment, another bearing, i.e., a third bearing, may be added towards the end of the shaft 660 near the lower impeller 654 to add additional support. In another alternative embodiment, rather than adding a third bearing, one of the bearings 644 or 646 within the motor housing 642 may be maintained in its position and the other of the bearings 644 or 646 may be moved towards the end of the shaft 660 near the lower impeller 654 to add additional support. However, other bearing arrangements are possible.

In this embodiment, the blower 600 may be supported within an outer casing 615 (e.g., forming a portion of a NIVV device such as a PAP device) by a support system. The support system includes side supports 624 to support the sides of the blower 600 and a bottom support 626 to support the bottom of the blower 600.

The side and bottom supports 624, 626 may be flexible members, e.g., elastomer, to isolate the blower 600 from the outer casing 615, e.g., vibration isolated. As illustrated, the side supports 624 are adapted to engage respective pegs 635 provided to the blower 600. The bottom support 626 provides a conduit from the outlet 620 of the blower 600 to the outlet 617 of the outer casing 615 (e.g., which may connectable to an air delivery conduit to deliver pressurized air to a patient for therapy).

8. Other Comments

While the invention has generally been described in terms of a centrifugal pump, it is not limited to this form, and may also take the form of a mixed flow type.

An aspect of the invention is that the chamber that defines the airflow path is generally axially symmetric. This does not mean that the entire airflow path of the device that uses a blower in accordance with the invention must also be axially symmetric. Variations within the scope of the present invention may include some asymmetries. These asymmetries may lie in a region where velocities are low such that losses and noise are less affected.

In an embodiment, the blower allows the airflow feed pattern through the impeller, and in the volute, to remain symmetrical irrespective of the flow rates. This results in lower levels of blade pass tonal noise emission, and lower levels of turbulence noise emission.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A blower for providing a supply of air at positive pressure in a range of approximately $2 cmH_2O$ to $30 cmH_2 0$, the blower comprising:
   a motor having a shaft,
   wherein the shaft includes a shaft axis;
   at least one impeller attached to the shaft; and
   a stationary component including a structure that surrounds the at least one impeller and the motor, the stationary component comprising an inlet and an outlet between which forms a flow path for a flow of air,
   wherein the shaft axis, the inlet, and the outlet are co-axial,
   wherein the motor includes a first side proximal the inlet and a second side distal the inlet,
   wherein the stationary component is configured to direct the flow of air to flow around the motor from the first side to the second side, and
   wherein at least a portion of the motor is configured to be exposed to the flow path extending from the inlet to the outlet such that the flow of air along the flow path allows cooling of the motor as air flows through the stationary component.

2. The blower according to claim 1, wherein the stationary component includes at least one vane that directs air in a radial direction.

3. The blower according to claim 2, wherein the at least one vane directs air from a tangential direction to the radial direction.

4. The blower according to claim 1, wherein the stationary component includes at least one vane that directs air in an axial direction.

5. The blower according to claim 4, wherein the at least one vane directs air from a tangential direction to the axial direction.

6. A non-invasive ventilation (NIVV) device comprising the blower according to claim 2.

7. The blower according to claim 1, wherein the impeller includes a plurality of blades adapted to accelerate air tangentially and to direct the air radially outward.

8. The blower according to claim 7, wherein the plurality of blades are sandwiched between a first disk-like shroud and a second disk-like shroud.

9. The blower according to claim 8, wherein the first disk-like shroud includes an outer diameter that is smaller compared to an outer diameter of the second disk-like shroud.

10. The blower according to claim 8, wherein the first disk-like shroud overlaps an inner portion of the plurality of blades of the impeller and includes a hub that is adapted to receive the shaft.

11. The blower according to claim 8, wherein the second disk-like shroud includes a center opening and extends to radially outer tips of the plurality of blades of the impeller.

12. The blower according to claim 7, wherein each of the plurality of blades has a continuously curved shape.

13. The blower according to claim 7, wherein each of the plurality of blades is tapered in width in radially outer portions.

14. The blower according to claim 7, wherein each of the plurality of blades has an inlet angle with respect to a tangent of between 0 degrees and 90 degrees.

15. The blower according to claim 7, wherein each of the plurality of blades has an outlet angle with respect to a tangent of between 70 degrees and 110 degrees.

16. The blower according to claim 1, wherein at least a portion of the flow path formed by the stationary component is an annular flow path, and the stationary component includes a plurality of stator vanes to receive air exiting the annular flow path, and each of the plurality of stator vanes has a stator vane leading edge located inwards radially relative to the annular flow path.

17. The blower according to claim 16, wherein the annular flow path is formed between an exterior surface of the motor and an interior surface of the stationary component.

18. The blower according to claim 16, further comprising a shield constructed and arranged such that there is not a line-of-sight path between the plurality of stator vanes and blades of the impeller.

19. The blower according to claim 1, wherein the first side is provided on an axial side of the motor proximal the inlet, and the second side is provided on an opposite axial side of the motor which is axially offset from the first side.

20. The blower according to claim 1, wherein the motor includes a stator assembly, and wherein at least a portion of the stator assembly is configured to be exposed to the flow of air along the flow path which allows cooling of the stator assembly as air flows through the stationary component.

21. The blower according to claim 1, wherein the motor includes an external wall, and wherein at least a portion of the external wall is configured to be exposed to the flow of air along the flow path which allows cooling of the motor as air flows through the stationary component.

22. The blower according to claim 1, wherein at least a portion of the flow path extending from the inlet to the outlet is formed between an exterior surface of the motor and an interior surface of the stationary component, where said portion of the flow path is annular, wherein the at least one impeller is located adjacent the first side of the motor and the stationary component includes a stator vane structure located adjacent the second side of the motor configured to receive air exiting said portion of the flow path, and wherein said portion of the flow path is configured to direct air to flow in an axial direction from the at least one impeller to the stator vane structure.

23. The blower according to claim 1, wherein the flow of air passes along the flow path from the inlet, past the at least one impeller, past the portion of the motor, and to the outlet.

24. The blower according to claim 1, wherein the stationary component is configured such that flow of air that passes along the portion of the motor is directed directly towards the outlet.

* * * * *

UNITED STATES PATENT AND TRADEMARK OFFICE
CERTIFICATE OF CORRECTION

| | | |
|---|---|---|
| PATENT NO. | : 11,892,000 B2 | |
| APPLICATION NO. | : 17/752992 | |
| DATED | : February 6, 2024 | |
| INVENTOR(S) | : Kenyon et al. | |

It is certified that error appears in the above-identified patent and that said Letters Patent is hereby corrected as shown below:

In the Claims

Column 15, Line 14, Claim 6, delete "claim 2" and insert --claim 1--.

Signed and Sealed this
Thirtieth Day of April, 2024

Katherine Kelly Vidal
*Director of the United States Patent and Trademark Office*